(12) United States Patent
Hestad et al.

(10) Patent No.: US 12,144,632 B2
(45) Date of Patent: *Nov. 19, 2024

(54) ELECTRODE CONNECTION AND METHOD THEREFOR

(71) Applicant: GREATBATCH LTD., Clarence, NY (US)

(72) Inventors: Hugh D. Hestad, Edina, MN (US); Jeff Fleigle, Brooklyn Park, MN (US); Christopher Mauhar, Maple Grove, MN (US); Krishna Vedula, Plymouth, MN (US); Hitesh Mehta, Plymouth, MN (US); Rommy U. Huleis, Littleton, CO (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/228,748

(22) Filed: Aug. 1, 2023

(65) Prior Publication Data

US 2023/0404459 A1 Dec. 21, 2023

Related U.S. Application Data

(63) Continuation of application No. 17/527,341, filed on Nov. 16, 2021, now Pat. No. 11,813,063, which is a continuation of application No. 16/669,887, filed on Oct. 31, 2019, now Pat. No. 11,241,184.

(60) Provisional application No. 62/757,787, filed on Nov. 9, 2018.

(51) Int. Cl.
A61B 5/296 (2021.01)
A61N 1/05 (2006.01)

(52) U.S. Cl.
CPC .............. *A61B 5/296* (2021.01); *A61N 1/05* (2013.01)

(58) Field of Classification Search
CPC ... A61B 5/296; A61B 5/287; A61B 2562/125; A61B 5/6851; A61B 5/6852; A61N 1/05; H01R 4/187; H01R 11/11
See application file for complete search history.

(56) References Cited

U.S. PATENT DOCUMENTS

| | | |
|---|---|---|
| 4,314,095 A | 2/1982 | Moore et al. |
| 6,181,971 B1 | 1/2001 | Doan |
| 6,421,569 B1 | 7/2002 | Treaba et al. |
| 7,047,081 B2 | 5/2006 | Kuzma et al. |
| 7,160,156 B2 | 1/2007 | Holliday |
| 7,650,184 B2 | 1/2010 | Walter |
| 7,957,818 B2 | 6/2011 | Swoyer |
| 8,011,980 B2 | 9/2011 | Conger |
| 8,280,528 B2 | 10/2012 | Kuzma et al. |
| 8,406,896 B2 | 3/2013 | McDonald et al. |
| 8,473,075 B2 | 6/2013 | Gallegos et al. |
| 8,594,761 B2 | 11/2013 | Victorine et al. |
| 8,600,518 B2 | 12/2013 | Meadows et al. |
| 8,639,355 B2 | 1/2014 | Soltis |
| 8,726,499 B2 | 5/2014 | McGiboney et al. |

(Continued)

*Primary Examiner* — Mark W. Bockelman
(74) *Attorney, Agent, or Firm* — Michael P. Horvath

(57) ABSTRACT

In various examples, a component for a medical device is described. The component includes a conductor wire including a connection portion. An electrode is formed from a conductive tube. The conductive tube is compressed at least partially around the connection portion of the conductor wire to at least partially surround and couple to the connection portion.

20 Claims, 7 Drawing Sheets

(56) References Cited

U.S. PATENT DOCUMENTS

| | | |
|---|---|---|
| 8,872,028 B2 | 10/2014 | Ito |
| 9,033,869 B2 | 5/2015 | Thenuwara et al. |
| 9,056,196 B2 | 6/2015 | Thenuwara et al. |
| 9,079,012 B2 | 7/2015 | Johnson et al. |
| 9,649,488 B2 | 5/2017 | Jadwizak et al. |
| 11,241,184 B2 * | 2/2022 | Hestad .................. A61B 5/296 |
| 11,813,063 B2 * | 11/2023 | Hestad .................. A61B 5/296 |
| 2002/0128700 A1 | 9/2002 | Cross |
| 2007/0027512 A1 | 2/2007 | Chan et al. |

* cited by examiner

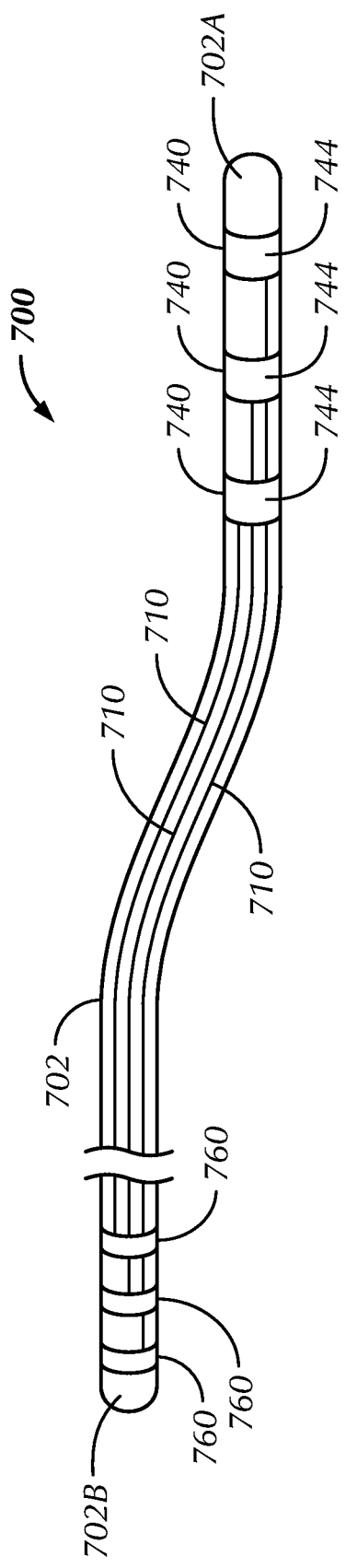
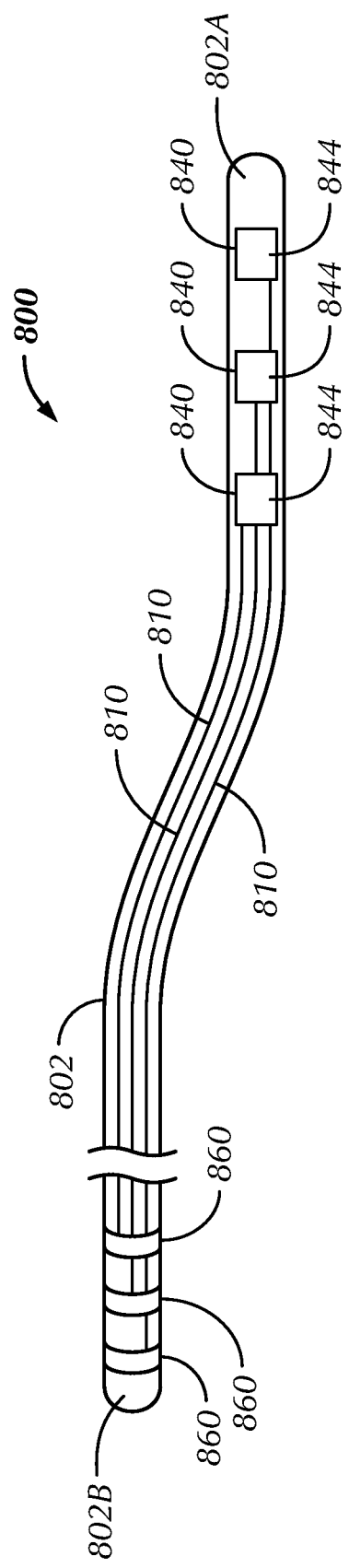
FIG. 7
FIG. 8

ELECTRODE CONNECTION AND METHOD THEREFOR

CROSS REFERENCE TO RELATED APPLICATIONS

This application is a continuation of and claims the benefit of priority under 35 U.S.C. § 120 to Hestad et al., U.S. patent application Ser. No. 17/527,341, now U.S. Pat. No. 11,813,063, filed on Nov. 16, 2021, entitled "ELECTRODE CONNECTION AND METHOD THEREFOR," which is a continuation of and claims the benefit of priority under 35 U.S.C. § 120 to Hestad et al., U.S. patent application Ser. No. 16/669,887, now U.S. Pat. No. 11,241,184, filed on Oct. 31, 2019, entitled "ELECTRODE CONNECTION AND METHOD THEREFOR," which claims the benefit of priority to U.S. Provisional Application Ser. No. 62/757,787, filed on Nov. 9, 2018, entitled "ELECTRODE CONNECTION," each of which is incorporated by reference herein in its entirety.

BACKGROUND

In lead or catheter construction, lead wires are connected to exposed electrodes on the outside of the lead or catheter. The electrodes are exposed to the patient and the lead wires are most often insulated and contained within the lead or catheter body. The lead wires create an electrical pathway from the proximal connection to the exposed electrodes. The lead wires are generally welded to the electrodes by means of laser or resistance welds. The welded areas are the sites of high heat (needed to fuse the metals), which create a heat affected zone (HAZ) that degrades the mechanical properties of the wires. In flexible leads, during normal use, the wire in the HAZ can bend and prematurely break, thereby potentially disrupting the electrical connection to the electrode. The problem also exists in pad and cuff style electrodes.

OVERVIEW

This overview is intended to provide an overview of subject matter of the present patent document. It is not intended to provide an exclusive or exhaustive explanation of the invention. The detailed description is included to provide further information about the present patent document.

The present inventors have recognized, among other things, that the present subject matter can be used in a device to connect a conductor wire to an electrode. Such a device includes, but is not limited to, a medical device. In various examples, the present subject matter is advantageous in that it provides for a connection between the conductor wire and the electrode in a manner that can inhibit premature breakage of the conductor wire or breakage of the conductor wire from the electrode. In some examples, the present subject matter inhibits breakage of the conductor wire and/or the connection between the conductor wire and the electrode within a heat affected zone (HAZ). To better illustrate the devices described herein, a non-limiting list of examples is provided here:

Example 1 can include subject matter that can include a component for a medical device. The component includes a conductor wire including a connection portion. An electrode is formed from a conductive tube, wherein the conductive tube is compressed at least partially around the connection portion of the conductor wire to at least partially surround and couple to the connection portion.

In Example 2, the subject matter of Example 1 is optionally configured such that the connection portion of the conductor wire is disposed proximate a distal end of the conductor wire.

In Example 3, the subject matter of Example 1 or 2 is optionally configured such that the connection portion is welded to the electrode.

In Example 4, the subject matter of Example 3 is optionally configured such that the connection portion is laser welded to the electrode.

In Example 5, the subject matter of Example 3 is optionally configured such that the connection portion is resistance welded to the electrode.

In Example 6, the subject matter of any one of Examples 1-5 is optionally configured such that the conductive tube is compressed such that the electrode formed is substantially U-shaped.

In Example 7, the subject matter of any one of Examples 1-5 is optionally configured such that the conductive tube is compressed such that the electrode formed is substantially T-shaped.

In Example 8, the subject matter of any one of Examples 1-7 is optionally configured such that the medical device includes an elongate lead, wherein the electrode is disposed within the lead with at least an electrode surface being exposed to an exterior of the lead.

In Example 9, the subject matter of any one of Examples 1-7 is optionally configured such that the medical device includes an elongate catheter, wherein the electrode is disposed within the catheter with at least an electrode surface being exposed to an exterior of the catheter.

In Example 10, the subject matter of any one of Examples 1-9 is optionally configured such that the conductive tube is compressed into direct contact with the conductor wire.

In Example 11, the subject matter of any one of Examples 1-10 optionally includes a coupling tube, wherein the conductive tube is compressed into direct contact with the coupling tube. The conductor wire is at least partially disposed within the coupling tube.

In Example 12, the subject matter of Example 11 is optionally configured such that the conductor wire is coupled to the coupling tube.

In Example 13, the subject matter of Example 11 or 12 is optionally configured such that the conductor wire is welded to the coupling tube.

In Example 14, the subject matter of any one of Examples 1-13 is optionally configured such that the conductive tube includes an inner surface facing inwardly toward an axis of the conductive tube and an outer surface facing outwardly away from the axis of the conductive tube. The connection portion of the conductor wire is coupled to a first portion of the inner surface, wherein the electrode includes the conductive tube collapsed such that at least the first portion of the inner surface and the connection portion of the conductor wire contacts at least a second portion of the inner surface to substantially sandwich the connection portion of the conductor wire between the first portion of the inner surface and the second portion of the inner surface.

In Example 15, the subject matter of any one of Examples 1-14 is optionally configured such that the conductive tube is compressed at least partially around the connection portion of the conductor wire to constrain motion of the connection portion of the conductor wire relative to the conductive tube.

In Example 16, the subject matter of any one of Examples 1-15 is optionally configured such that the electrode includes a rounded surface configured to contact and stimulate tissue of a patient.

In Example 17, the subject matter of any one of Examples 1-16 is optionally configured such that the electrode includes a substantially flat surface configured to contact and stimulate tissue of a patient.

In Example 18, the subject matter of any one of Examples 1-17 is optionally configured such that the conductive tube is folded at least partially around the connection portion of the conductor wire to form the electrode.

In Example 19, the subject matter of Example 18 is optionally configured such that the conductive tube is folded at least partially around a coupling tube within which the connection portion of the conductor wire is disposed to form the electrode.

Example 20 can include, or can optionally be combined with any one of Examples 1-19 to include subject matter that can include a component for a medical device. The component includes a conductor wire including a connection portion. An electrode is formed from a conductive tube, wherein the conductive tube includes an inner surface facing inwardly toward an axis of the conductive tube and an outer surface facing outwardly away from the axis of the conductive tube. The connection portion of the conductor wire is coupled to a first portion of the inner surface, wherein the electrode includes the conductive tube collapsed such that at least the first portion of the inner surface and the connection portion of the conductor wire contacts at least a second portion of the inner surface to substantially sandwich the connection portion of the conductor wire between the first portion of the inner surface and the second portion of the inner surface.

In Example 21, the subject matter of Example 20 is optionally configured such that the conductive tube is collapsed such that the electrode formed is substantially U-shaped.

In Example 22, the subject matter of Example 20 is optionally configured such that the conductive tube is collapsed such that the electrode formed is substantially T-shaped.

In Example 23, the subject matter of any one of Examples 20-22 is optionally configured such that the connection portion is welded to the electrode.

In Example 24, the subject matter of any one of Examples 20-23 is optionally configured such that the connection portion is laser welded to the electrode.

In Example 25, the subject matter of any one of Examples 20-23 is optionally configured such that the connection portion is resistance welded to the electrode.

In Example 26, the subject matter of any one of Examples 20-25 is optionally configured such that the connection portion of the conductor wire is disposed proximate a distal end of the conductor wire.

In Example 27, the subject matter of any one of Examples 20-26 is optionally configured such that the conductive tube is compressed into direct contact with the conductor wire.

In Example 28, the subject matter of any one of Examples 20-27 optionally includes a coupling tube, wherein the conductive tube is compressed into direct contact with the coupling tube. The conductor wire is at least partially disposed within the coupling tube.

In Example 29, the subject matter of Example 28 is optionally configured such that the conductor wire is coupled to the coupling tube.

In Example 30, the subject matter of Example 28 or 29 is optionally configured such that the conductor wire is welded to the coupling tube.

In Example 31, the subject matter of any one of Examples 20-30 is optionally configured such that the conductive tube is compressed at least partially around the connection portion of the conductor wire to constrain motion of the connection portion of the conductor wire relative to the conductive tube.

In Example 32, the subject matter of any one of Examples 20-31 is optionally configured such that the conductor wire includes a conductor coil.

Example 33 can include, or can optionally be combined with any one of Examples 1-32 to include subject matter that can include a method of forming a component for a medical device. The method includes placing a connection portion of a conductor wire in contact with a conductive tube. An electrode is formed by compressing the conductive tube at least partially around the connection portion of the conductor wire to at least partially surround and couple to the connection portion.

In Example 34, the subject matter of Example 33 is optionally configured such that forming the electrode includes compressing the conductive tube such that the electrode formed is substantially U-shaped.

In Example 35, the subject matter of Example 33 is optionally configured such that forming the electrode includes compressing the conductive tube such that the electrode formed is substantially T-shaped.

In Example 36, the subject matter of any one of Examples 33-35 is optionally configured such that forming the electrode includes compressing the conductive tube into direct contact with the conductor wire.

In Example 37, the subject matter of any one of Examples 33-36 optionally includes welding the connection portion of the conductor wire to the electrode.

In Example 38, the subject matter of Example 37 is optionally configured such that welding the connection portion includes laser welding the connection portion to the electrode.

In Example 39, the subject matter of Example 37 is optionally configured such that welding the connection portion includes resistance welding the connection portion to the electrode.

In Example 40, the subject matter of any one of Examples 33-40 is optionally configured such that the conductive tube includes an inner surface facing inwardly toward an axis of the conductive tube and an outer surface facing outwardly away from the axis of the conductive tube. The connection portion of the conductor wire is coupled to a first portion of the inner surface, wherein compressing the conductive tube includes compressing the conductive tube such that at least the first portion of the inner surface and the connection portion of the conductor wire contacts at least a second portion of the inner surface to substantially sandwich the connection portion of the conductor wire between the first portion of the inner surface and the second portion of the inner surface.

In Example 41, the subject matter of any one of Examples 33-40 is optionally configured such that forming the electrode includes compressing the conductive tube at least partially around the connection portion of the conductor wire to constrain motion of the connection portion of the conductor wire relative to the conductive tube.

In Example 42, the subject matter of any one of Examples 33-41 is optionally configured such that forming the electrode includes compressing the conductive tube into direct contact with a coupling tube, the conductor wire being at least partially disposed within the coupling tube.

In Example 43, the subject matter of Example 42 optionally includes coupling the conductor wire to the coupling tube.

In Example 44, the subject matter of Example 42 or 43 optionally includes welding the conductor wire to the coupling tube.

BRIEF DESCRIPTION OF THE DRAWINGS

FIG. 7 is a side view of a distal end of a lead with electrodes in accordance with at least one example of the invention.

FIG. 8 is a side view of a distal end of a lead with electrodes in accordance with at least one example of the invention.

DETAILED DESCRIPTION

Figure 1A:
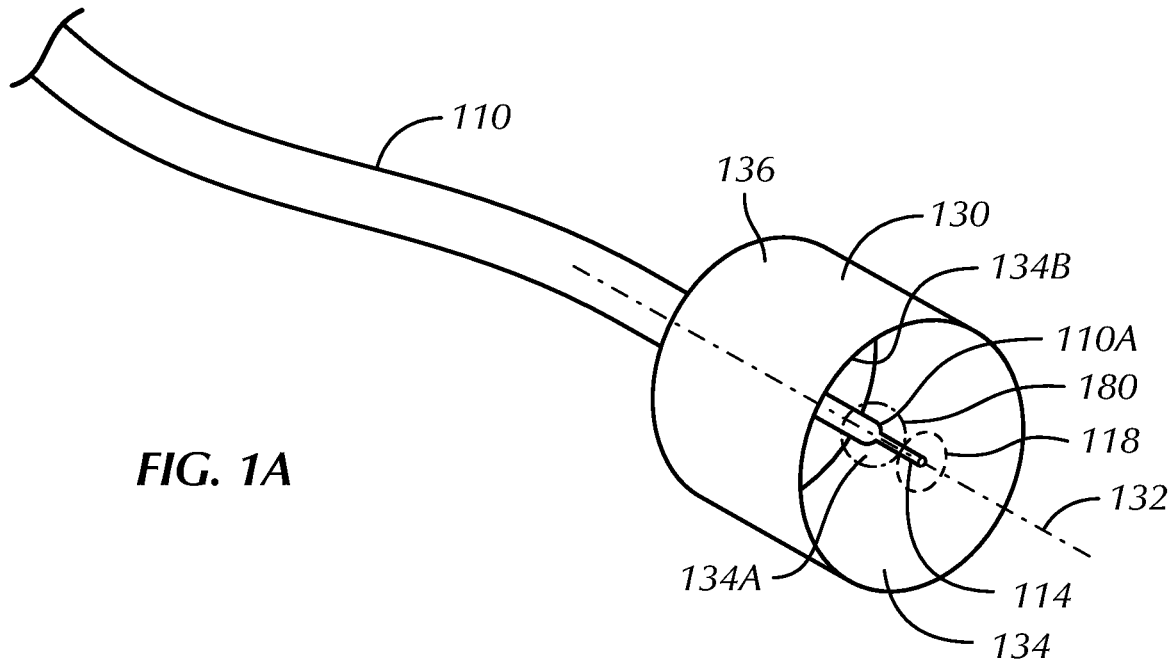
FIGS. 1A and 1B show formation of an electrode in accordance with at least one example of the invention.

The present invention relates generally to providing a robust connection between a conductor wire and an electrode in a device. More specifically, the present invention relates to the use of a connection between a conductor wire and an electrode that inhibits breakage of the conductor wire and/or separation of the conductor wire from the electrode, particularly within a heat affected zone (HAZ). As such, it is contemplated herein that the present subject matter can be used within a device to inhibit premature breakage of the conductor wire or breakage of the conductor wire from the electrode. In some examples, such a device can include a medical device; however, the present invention is not intended to be so limited as devices other than medical devices are contemplated herein.

In some examples, the purpose of the present invention is to connect a conductor wire to an electrode. In further examples, the conductor wire is connected to the electrode in a manner that can inhibit premature breakage of the conductor wire, such as, for instance breakage of the conductor wire within the HAZ. In some examples, an electrode connection is formed in which the conductor wire is welded to the electrode, and the electrode is then formed (for instance, collapsed down onto itself) to essentially sandwich the conductor wire between sides of the electrode.

The present subject matter is advantageous in many respects. For instance, in some examples, the present subject matter allows for faster production of a small electrode-to-wire connection and improved fatigue and durability characteristics of the electrode connection. In some examples, the present subject matter advantageously inhibits, if not avoids, flexing of the conductor wire in the weld HAZ. In some examples, the present subject matter can also inhibit, if not eliminate, the need for secondary welding due to a mechanical joint created during the forming of the electrode. That is, in some examples, forming of electrodes in conjunction with conductors creates a mechanical connection to the electrode, which can potentially eliminate welds, or, if welds are used, shield welds in the HAZ to reduce the likelihood of fracture of the conductor wire.

In various examples, the present subject matter includes a connection between a conductor wire and an electrode that reduces, if not eliminates, a chance of the conductor wire separating from the electrode, for instance, due to breakage of the conductor wire in the HAZ. In other examples, the present subject matter includes a device or apparatus including one or more of such connections. In still other examples, the present subject matter includes a method of making such a connection between a conductor wire and an electrode.

In some examples, the present subject matter can be used for one or more electrodes in an elongate device, such as, for instance a medical device. In some examples, the medical device includes an at least partially implantable medical device. In further examples, the present subject matter can be used for one or more electrodes in a lead. In other examples, the present subject matter can be used for one or more electrodes in a catheter.

In various examples described herein, electrodes can be formed, at least in part, from platinum. In other examples, the electrodes described can be formed from one or more materials, either in addition to or instead of platinum, provided the materials are biocompatible and configured to properly function to conduct electrical signals between the electrode and tissue (including one or more of muscle tissue, nervous tissue, epithelial tissue, and/or connective tissue) of the patient. In some examples, the electrodes described herein are shaped to form directional electrodes to allow stimulation from the electrodes to be directed in a specific path from the example medical devices within which the one or more electrodes are disposed.

In various examples described herein, conductor wires can be formed, at least in part, from a nickel-cobalt alloy, such as, but not limited to, MP35N. In other examples, the conductor wires described can be formed from one or more materials, either in addition to or instead of a nickel-cobalt alloy, provided the materials are configured to properly function to conduct electrical signals between a pulse generator or other medical device and the electrode.

Figure 1B:
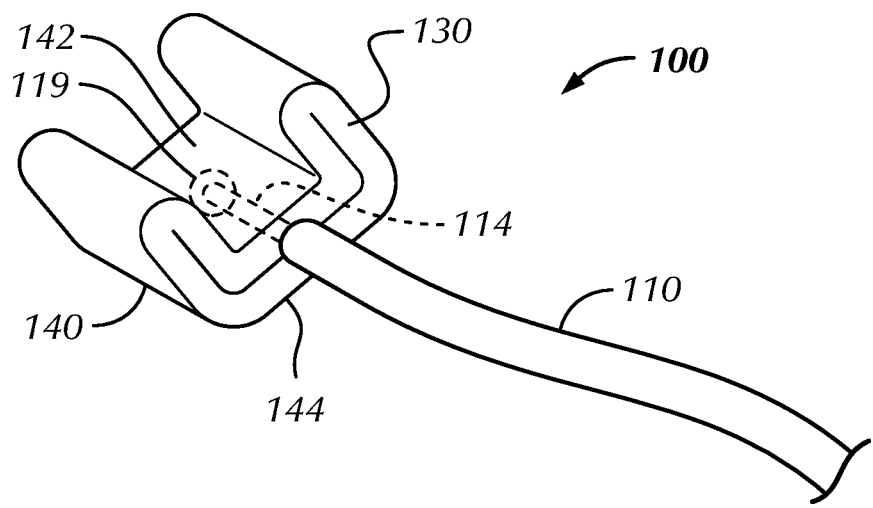

Referring to FIGS. 1A and 1B, in some examples, a component 100 is configured to be used with a medical device. In some examples, the component includes a conductor wire 110 coupled to an electrode 140. The conductor wire 110, in some examples, includes a proximal end (not shown), which, in various examples, can be coupled to electronic modules (in an external control unit, an implantable device, or the like) to control operation of the electrode 140. In some examples, the conductor wire 110 includes a connection portion 114 configured for connection to the electrode 140. That is, in some examples, the connection portion 114 includes no insulation or at least insulation partially removed (that is, a stripped or partially stripped portion of the conductor wire 110, such that bare wire of the conductor wire 110 is exposed) in order to facilitate at least a reliable and contaminant-free electrical (if not also mechanical) connection of the conductor wire 110 to the electrode 140. In other examples, the connection portion 114 can be an insulated portion of the conductor wire 110 and formation of the of the electrode 140 and/or the component 100 can enable an electrical connection between the connection portion 114 and the electrode 140. That is, in some examples, welding of the connection portion 114 to the electrode 140 vaporizes or otherwise at least partially removes the insulation of the connection portion 114, thereby allowing the connection portion 114 to be electrically coupled to the electrode 140. In other examples, either instead of or in addition to welding of the connection portion 114 to the electrode 140, compression of the electrode 140 onto the connection portion 114 of the conductor wire 110 punctures, strips, or otherwise breaches at least some of the insulation of the connector portion 114 to allow electrical coupling of the connection portion 114 to the electrode 140. In some examples, the connection portion 114 is disposed proximate a distal end 110A of the conductor wire 110. In other examples, the connection portion can be disposed at a portion of the conductor wire 110 intermediate the proximal end and the distal end 110A of the conductor wire 110. In further examples, the conductor wire 110 can include two or more connection portions disposed along the conductor wire 110, for instance, to couple two or more electrodes 140 to the conductor wire 110.

In some examples, the electrode 140 is formed from a conductive tube 130. In some examples, the conductive tube 130 can include a substantially cylindrical tube. In other examples, the conductive tube can include a differently shaped tube, including, but not limited to an oval-shaped tube, a box-shaped tube, a triangular-shaped tube, or the like. In still other examples, instead of a conductive tube, the electrode can be formed from a non-tubular substantially planar conductive sheet. In some examples, the conductive tube 130 is compressed at least partially around the connection portion 114 of the conductor wire 110 to at least partially surround and couple to the connection portion 114. In some examples, the compressing of the conductive tube 130 around the connection portion 114 mechanically couples the connection portion 114 of the conductor wire 110 to the conductive tube 130. In further examples, the compressing of the conductive tube 130 around the connection portion 114 also electrically couples the connection portion 114 of the conductor wire 110 to the conductive tube 130. Alternatively, or in addition thereto, in some examples, the connection portion 114 can be welded to the conductive tube 130 prior to compression of the conductive tube 130 (at weld 118) at least partially around the connection portion 114 of the conductor wire 110 and/or after compression of the conductive tube 130 (at weld 119) at least partially around the connection portion 114 of the conductor wire 110. In some examples, the connection portion 114 is laser welded to the conductive tube 130. In other examples, the connection portion 114 is resistance welded to the conductive tube 130. In this way, in some examples, the connector portion 114 of the conductor wire 110 is mechanically and electrically coupled to the conductive tube 130.

In some examples, as described above, welding of the conductor wire 110 to the conductive tube 130 at the weld 118 prior to compression of the conductive tube 130 at least partially around the connection portion 114 of the conductor wire 110 can create a heat affected zone (HAZ) 180. The conductor wire 110 within the HAZ 180, in some examples, can become more brittle and/or have an increased chance of breakage than a portion of the conductor wire 110 that is not within the HAZ 180. The present subject matter seeks to reduce the chances of such breakage of the conductor wire 110 and/or disconnection of the conductor wire 110 from the electrode 140 in the manners described herein.

In some examples, the conductive tube 130 is compressed into direct contact with the conductor wire 110. That is, in some examples, sides of the conductive tube 130 are pushed together to trap at least a portion of the conductor wire 110, and, namely, the connection portion 114 of the conductor wire 110, between the sides of the conductive tube 130, to thereby at least mechanically couple the conductor wire 110 to the conductive tube 130. In some examples, referring specifically to FIG. 1B, the conductive tube 130 is compressed such that the electrode 140 formed is substantially U-shaped. In some examples, the U-shaped conductive tube 130 forms the finished electrode 140. In other examples, the U-shaped conductive tube 130 is further formed, folded, and/or manipulated into the intended shape for the electrode 140, depending upon space constraints, a geometry, a size, a purpose, etc. of a device within which the electrode 140 is to be used. As such, other shapes of the electrode are contemplated in other examples, at least some of which are described below. In some examples, the electrode 140 includes a substantially flat surface 144 configured to contact and stimulate tissue (including one or more of muscle tissue, nervous tissue, epithelial tissue, and/or connective tissue) of a patient and/or sense a physiological signal or condition. That is, the electrode 140 includes a substantially boxed-off U-shaped configuration included substantially squared-off corners.

In some examples, the conductive tube 130 includes an inner surface 134 facing inwardly toward an axis 132 of the conductive tube 130 and an outer surface 136 facing outwardly away from the axis 132 of the conductive tube 130. In some examples, the connection portion 114 of the conductor wire 110 is coupled to a first portion 134A of the inner surface 134. In some examples, the electrode 140 includes the conductive tube 130 collapsed such that at least the first portion 134A of the inner surface 134 and the connection portion 114 of the conductor wire 110 contact at least a second portion 134B of the inner surface 134 to substantially sandwich the connection portion 114 of the conductor wire 110 between the first portion 134A of the inner surface 134 and the second portion 134B of the inner surface 134. In some examples, the conductive tube 130 is folded at least partially around the connection portion 114 of the conductor wire 110 to form the electrode 140. In some examples, the conductive tube 130 is compressed at least partially around the connection portion 114 of the conductor wire 110 to constrain motion of the connection portion 114 of the conductor wire 110 relative to the conductive tube 130. In some examples, the connection portion 114 is welded at the weld 119 to the electrode 140 after the conductive tube 130 is compressed to form the electrode 140. Welding at the weld 119 can be performed in addition to the weld 118 in some examples. In other examples, welding at the weld 119 can be performed instead of the weld 118. In some examples, the connection portion 114 is laser welded to the electrode 140. In other examples, the connection portion 114 is resistance welded to the electrode 140. In some examples, the weld 119 is performed at an exterior 142 of the electrode 140, the weld 119 passing through the conductive tube 130 to couple the connection portion 114 of the conductor wire 110 to the electrode 140.

If welded at the weld 118, brittleness of the connection portion 114 and/or the conductor wire 110 and the weld 118 can be counteracted by constraining motion of the connector portion 114 with respect to the conductive tube 130. Limiting motion of the connection portion 114 relative to the conductive tube 130 reduces, if not eliminates, the chance of the weld 118, the connection portion 114, and/or the conductive tube 130 breaking, rupturing, or otherwise separating to disrupt the connection between the conductor wire 110 and the electrode 140 to disable the electrode 140 in the ultimate device in which the electrode 140 is used. In many cases, an implanted device (such as, for instance, an implantable lead in conjunction with an implantable pulse generator) in which an electrode fails must be explanted and replaced, which leads to increased cost and recovery due to the surgical procedure required for such explant and replacement. In other cases of temporary and/or partial implantation (for instance, a catheter temporarily implanted in order to access a location within a patient), an electrode failure can require the device to be removed and replaced with another device in order to perform the intended procedure. This can lead to increased procedure time, patient risk, and cost due to having to use multiple devices for one procedure. In this way, in some examples, the present subject matter increases the robustness of the electrode 140 and, in turn, increases reliability of the ultimate device with which the electrode 140 is being used.

Figure 2:
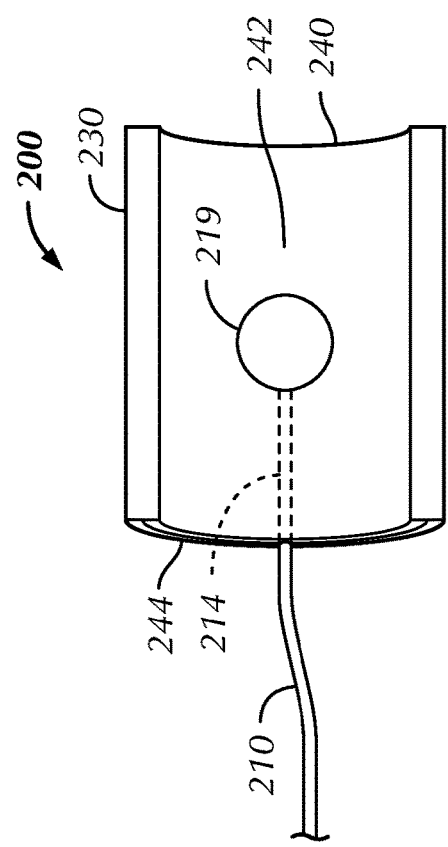
FIG. 2 is a perspective view of an electrode in accordance with at least one example of the invention.

Referring to FIG. 2, in some examples, a component 200 is configured to be used with a medical device. The component 200, in some examples, is similar in many respects to the component 100 described above, and, as such, at least some of the description of the component 100 above can also apply to the component 200. In some examples, the component includes a conductor wire 210 coupled to an electrode 240. In some examples, the electrode 240 is formed from a conductive tube 230. In some examples, the electrode 240 is formed in a manner similar to that described above with respect to the electrode 140. In some examples, the conductive tube 230 can include a substantially cylindrical tube. In other examples, the conductive tube can include a differently shaped tube, including, but not limited to an oval-shaped tube, a box-shaped tube, a triangular-shaped tube, or the like. In still other examples, instead of a conductive tube, the electrode can be formed from a non-tubular substantially planar conductive sheet. In some examples, the conductive tube 230 is compressed at least partially around a connection portion 214 of the conductor wire 210 to at least partially surround and couple to the connection portion 214. In some examples, the conductor wire 210 is similar to the conductor wire 110 described above. In some examples, the compressing of the conductive tube 230 around the connection portion 214 mechanically couples the connection portion 214 of the conductor wire 210 to the conductive tube 230. In further examples, the compressing of the conductive tube 230 around the connection portion 214 also electrically couples the connection portion 214 of the conductor wire 210 to the conductive tube 230. Alternatively, or in addition thereto, in some examples, the connection portion 214 can be welded to the conductive tube 230 prior to compression of the conductive tube 230 at least partially around the connection portion 214 of the conductor wire 210 and/or after compression of the conductive tube 230 (at weld 219) at least partially around the connection portion 214 of the conductor wire 210. In some examples, the connection portion 214 is laser welded to the conductive tube 230. In other examples, the connection portion 214 is resistance welded to the conductive tube 230. In this way, in some examples, the connector portion 214 of the conductor wire 210 is mechanically and electrically coupled to the conductive tube 230.

In some examples, as described above, welding of the conductor wire 210 to the conductive tube 230 prior to compression of the conductive tube 230 at least partially around the connection portion 214 of the conductor wire 210 can create a heat affected zone (HAZ). The conductor wire 210 within the HAZ, in some examples, can become more brittle and/or have an increased chance of breakage than a portion of the conductor wire 210 that is not within the HAZ. The present subject matter seeks to reduce the chances of such breakage of the conductor wire 210 and/or disconnection of the conductor wire 210 from the electrode 240 in the manners described herein.

In some examples, the conductive tube 230 is compressed into direct contact with the conductor wire 210. That is, in some examples, sides of the conductive tube 230 are pushed together to trap at least a portion of the conductor wire 210, and, namely, the connection portion 214 of the conductor wire 210, between the sides of the conductive tube 230, to thereby at least mechanically couple the conductor wire 210 to the conductive tube 230. In some examples, the conductive tube 230 is compressed such that the electrode 240 formed is substantially U-shaped. In some examples, the U-shaped conductive tube 230 forms the finished electrode 240. In other examples, the U-shaped conductive tube 230 is further formed, folded, and/or manipulated into the intended shape for the electrode 240, depending upon space constraints, a geometry, a size, a purpose, etc. of a device within which the electrode 240 is to be used. As such, other shapes of the electrode are contemplated in other examples, at least some of which are described below. In some examples, the electrode 240 includes a rounded surface 244 configured to contact and stimulate tissue (including one or more of muscle tissue, nervous tissue, epithelial tissue, and/or connective tissue) of a patient and/or sense a physiological signal or condition. That is, the electrode 240 includes a rounded substantially U-shaped configuration. In some examples, the shape of the electrode 240 is substantially semicircular in cross section. In this regard, in some examples, the component 200 is largely similar to the component 100 but for the ultimate shape of the electrode 240.

In some examples, the conductive tube 230 is folded at least partially around the connection portion 214 of the conductor wire 210 to form the electrode 240. In some examples, the conductive tube 230 is compressed at least partially around the connection portion 214 of the conductor wire 210 to constrain motion of the connection portion 214 of the conductor wire 210 relative to the conductive tube 230. In some examples, the connection portion 214 is welded at the weld 219 to the electrode 240 after the conductive tube 230 is compressed to form the electrode 240. In some examples, the connection portion 214 is laser welded at the weld 219 to the electrode 240. In other examples, the connection portion 214 is resistance welded at the weld 219 to the electrode 240. In some examples, the weld 219 is performed at an exterior 242 of the electrode 240, the weld 219 passing through the conductive tube 230 to couple the connection portion 214 of the conductor wire 210 to the electrode 240.

In this way, in various examples, motion of the connection portion 214 relative to the conductive tube 230 is limited, thereby reducing, if not eliminating, the chance of the connection portion 214 and/or the conductive tube 230 breaking, rupturing, or otherwise separating to disrupt the connection between the conductor wire 210 and the electrode 240 to disable the electrode 240 in the ultimate device in which the electrode 240 is used. In this way, in some examples, the present subject matter increases the robustness of the electrode 240 and, in turn, increases reliability of the ultimate device with which the electrode 240 is being used.

Figure 3:
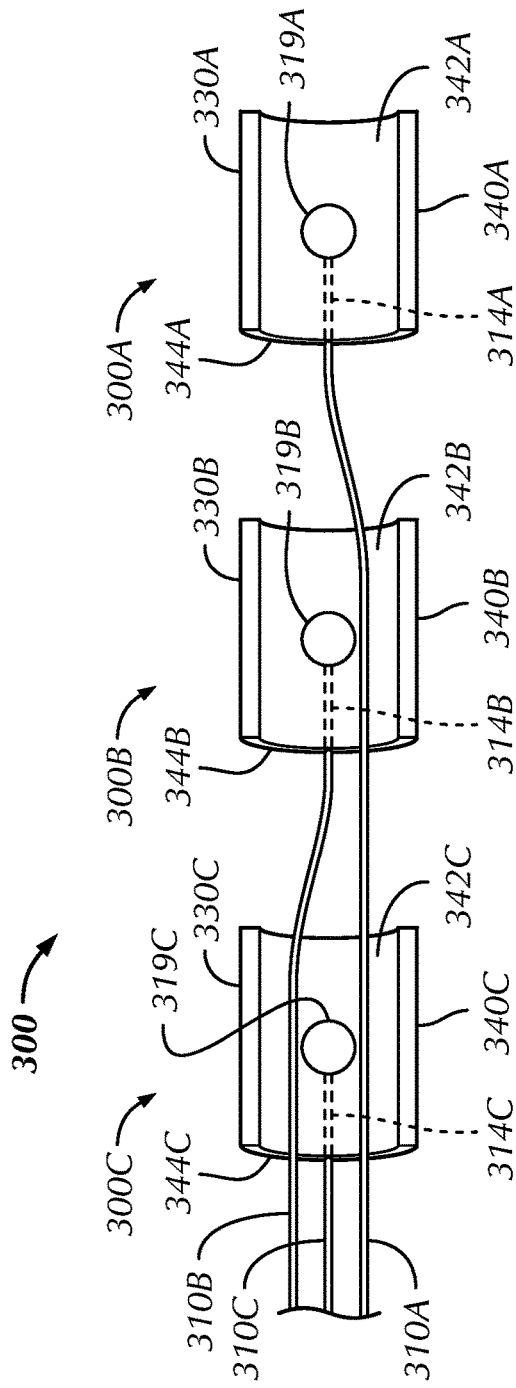
FIG. 3 is a perspective view of a series of electrodes in accordance with at least one example of the invention.

Referring now to FIG. 3, an assembly 300 includes two or more components 300A, 300B, 300C. In the example shown in FIG. 3, the assembly 300 includes three components 300A, 300B, 300C; however, this is merely illustrative as the component 300, in other examples, can include more or less than three components 300A, 300B, 300C. In some examples, the two or more components 300A, 300B, 300C are similar in many respects to the component 100 and/or the component 200 described above, and, as such, at least some of the description of the components 100, 200 above can also apply to the two or more components 300A, 300B, 300C. In some examples, each of the components 300A, 300B, 300C includes a conductor wire 310A, 310B, 310C coupled to an electrode 340A, 340B, 340C. In some examples, with the two or more components 300A, 300B, 300C of the assembly 300 used in an at least partially implantable elongate member such as, but not limited to, a catheter, a lead, a guidewire, or the like, the electrodes 340A, 340B, 340C of the assembly 300 can be used to stimulate tissue (including one or more of muscle tissue, nervous tissue, epithelial tissue, and/or connective tissue), sense physiological conditions, or a combination thereof.

In some examples, the electrodes 340A, 340B, 340C are each formed from conductive tubes 330A, 330B, 330C. In some examples, the electrodes 340A, 340B, 340C are formed in a manner similar to that described above with respect to the electrode 140 or the electrode 240. In some examples, each of the conductive tubes 330A, 330B, 330C are compressed at least partially around a connection portion 314A, 314B, 314C of each of the conductor wires 310A, 310B, 310C to at least partially surround and couple to the connection portion 314A, 314B, 314C. In some examples, the compressing of each of the conductive tubes 330A, 330B, 330C around the connection portions 314A, 314B, 314C, respectively, mechanically couples the connection portions 314A, 314B, 314C of the conductor wires 310A, 310B, 310C to the conductive tubes 330A, 330B, 330C. In further examples, the compressing of the conductive tubes 330A, 330B, 330C around the connection portions 314A, 314B, 314C, respectively, also electrically couples the connection portions 314A, 314B, 314C of the conductor wires 310A, 310B, 310C to the conductive tubes 330A, 330B, 330C. Alternatively, or in addition thereto, in some examples, one or more of the connection portions 314A, 314B, 314C can be welded to one or more of the conductive tubes 330A, 330B, 330C, respectively, prior to compression of the conductive tube 330A, 330B, 330C at least partially around the connection portion 314A, 314B, 314C of the conductor wire 310A, 310B, 310C and/or after compression of the conductive tube 330A, 330B, 330C (at weld 319A, 319B, 319C) at least partially around the connection portion 314A, 314B, 314C of the conductor wire 310A, 310B, 310C. In some examples, the two or more connection portions 314A, 314B, 314C are laser welded to the respective two or more conductive tubes 330A, 330B, 330C. In other examples, the two or more connection portions 314A, 314B, 314C are resistance welded to the respective two or more conductive tubes 330A, 330B, 330C. In this way, in some examples, the connector portions 314A, 314B, 314C of the conductor wires 310A, 310B, 310C are mechanically and electrically coupled to the respective conductive tubes 330A, 330B, 330C.

In some examples, the conductive tubes 330A, 330B, 330C are compressed into direct contact with the respective conductor wires 310A, 310B, 310C. That is, in some examples, sides of each of the conductive tubes 330A, 330B, 330C are pushed together to trap at least a portion of the respective conductor wire 310A, 310B, 310C, and, namely, the connection portion 314A, 314B, 314C of the conductor wire 310A, 310B, 310C, between the sides of the conductive tube 330A, 330B, 330C, to thereby at least mechanically couple the conductor wire 310A, 310B, 310C to the conductive tube 330A, 330B, 330C. In some examples, the conductive tube 330A, 330B, 330C is compressed such that the electrode 340A, 340B, 340C formed is substantially U-shaped. In some examples, the two or more U-shaped conductive tubes 330A, 330B, 330C form the two or more finished electrodes 340A, 340B, 340C. In other examples, the U-shaped conductive tube 330A, 330B, 330C is further formed, folded, and/or manipulated into the intended shape for the electrode 340A, 340B, 340C, depending upon space constraints, a geometry, a size, a purpose, etc. of a device within which the electrode 340A, 340B, 340C is to be used. As such, other shapes of the electrode are contemplated in other examples, at least some of which are described below. In some examples, the two or more electrodes 340A, 340B, 340C each include a rounded surface 344A, 344B, 344C configured to contact and stimulate tissue (including one or more of muscle tissue, nervous tissue, epithelial tissue, and/or connective tissue) of a patient and/or sense a physiological signal or condition. That is, in some examples, the two or more electrodes 340A, 340B, 340C each include a rounded substantially U-shaped configuration. In some examples, the shape of the two or more electrodes 340A, 340B, 340C is substantially semicircular in cross section. In this regard, in some examples, the two or more components 300A, 300B, 300C are largely similar to the component 200 described above. In other examples, the two or more electrodes 340A, 340B, 340C include at least one electrode that is differently shaped from at least another electrode, for instance, if such a configuration is beneficial with respect to a particular application.

In some examples, each of the conductive tubes 330A, 330B, 330C is folded at least partially around the respective connection portion 314A, 314B, 314C of the conductor wire 310A, 310B, 310C to form the electrode 340A, 340B, 340C. In some examples, the two or more conductive tubes 330A, 330B, 330C are compressed at least partially around the respective connection portions 314A, 314B, 314C of the conductor wires 310A, 310B, 310C to constrain motion of the connection portions 314A, 314B, 314C of the conductor wires 310A, 310B, 310C relative to the respective conductive tubes 330A, 330B, 330C. In some examples, each of the two or more connection portions 314A, 314B, 314C is welded at the weld 319A, 319B, 319C to the respective electrode 340A, 340B, 340C after the conductive tube 330A, 330B, 330C is compressed to form the electrode 340A, 340B, 340C. In some examples, each of the two or more connection portions 314A, 314B, 314C is laser welded at the weld 319A, 319B, 319C to the respective electrode 340A, 340B, 340C. In other examples, each of the two or more connection portions 314A, 314B, 314C is resistance welded at the weld 319A, 319B, 319C to the respective electrode 340A, 340B, 340C. In some examples, each of the welds 319A, 319B, 319C is performed at an exterior 342A, 342B, 342C of the electrode 340A, 340B, 340C, the welds 319A, 319B, 319C passing through the respective conductive tubes 330A, 330B, 330C to couple the connection portion 314A, 314B, 314C of the conductor wire 310A, 310B, 310C to the electrode 340A, 340B, 340C.

In this way, in various examples, motion of the two or more connection portions 314A, 314B, 314C relative to the respective conductive tubes 330A, 330B, 330C is limited, thereby reducing, if not eliminating, the chance of the connection portions 314A, 314B, 314C and/or the conductive tubes 330A, 330B, 330C breaking, rupturing, or otherwise separating to disrupt the respective connections between the conductor wires 310A, 310B, 310C and the electrodes 340A, 340B, 340C to disable any of the electrodes 340A, 340B, 340C in the ultimate device in which the electrodes 340A, 340B, 340C of the assembly 300 are used. In this way, in some examples, the present subject matter increases the robustness of the two or more electrodes 340A, 340B, 340C of the assembly 300 and, in turn, increases reliability of the ultimate device with which the electrodes 340A, 340B, 340C of the assembly 300 are being used.

Figure 4:
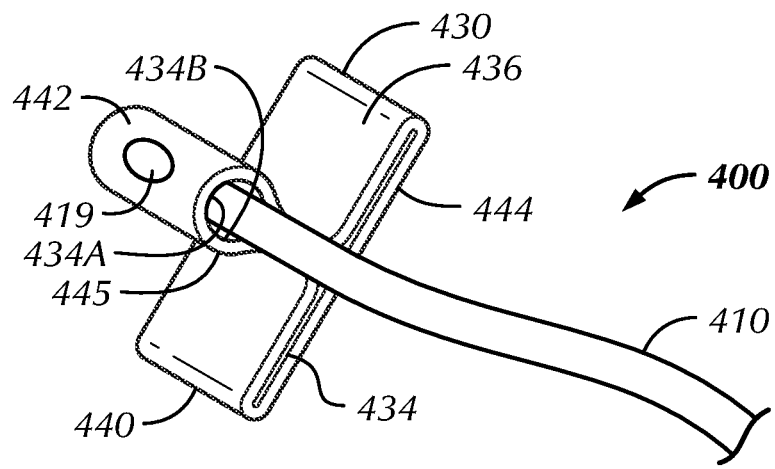
FIG. 4 is a perspective view of an electrode in accordance with at least one example of the invention.
Figure 5:
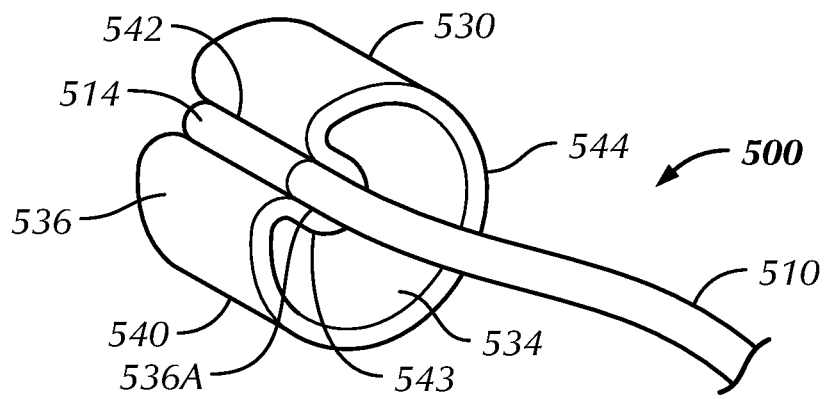
FIG. 5 is a perspective view of an electrode in accordance with at least one example of the invention.
Figure 6:
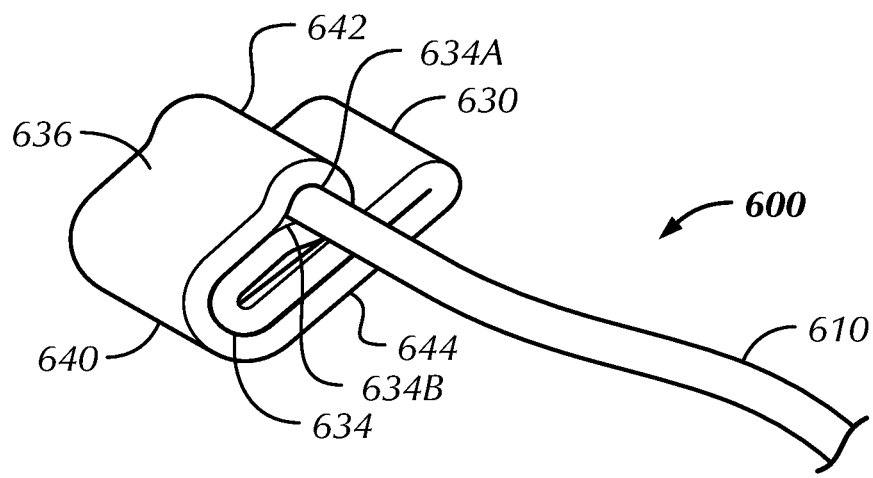
FIG. 6 is a perspective view of an electrode in accordance with at least one example of the invention.

Referring now to FIGS. 4-6, various examples of components 400, 500, 600 with differently-shaped electrodes 440, 540, 640 are shown. In some examples, one or more of the electrodes 440, 540, 640 can be used with the components 100, 200 and/or the assembly 300 described above, either in addition to, or instead of, the electrodes 140, 240, 340A, 340B, 340C described above. In some examples, the components 400, 500, 600 are similar in many respects to the component 100, the component 200, and/or the components 300A, 300B, 300C described above, and, as such, at least some of the description of the components 100, 200, 300A, 300B, 300C above can also apply to the components 400, 500, 600.

Referring specifically to FIG. 4, the component 400 includes the electrode 440 coupled to a conductor wire 410. In some examples, the electrode 440 is formed from a conductive tube 430. In some examples, the conductive tube 430 is compressed at least partially around a connection portion of the conductor wire 410 to at least partially surround and couple to the connection portion. In some examples, the compressing of the conductive tube 430 around the connection portion mechanically couples the connection portion of the conductor wire 410 to the conductive tube 430. In further examples, the compressing of the conductive tube 430 around the connection portion also electrically couples the connection portion of the conductor wire 410 to the conductive tube 430. Alternatively, or in addition thereto, in some examples, the connection portion can be welded to the conductive tube 430 prior to compression of the conductive tube 430 at least partially around the connection portion of the conductor wire 410 and/or after compression of the conductive tube 430 at least partially around the connection portion of the conductor wire 410. In some examples, the connection portion is laser welded to the conductive tube 430. In other examples, the connection portion is resistance welded to the conductive tube 430. In this way, in some examples, the connector portion of the conductor wire 410 is mechanically and electrically coupled to the conductive tube 430.

In some examples, as described above, welding of the conductor wire 410 to the conductive tube 430 prior to compression of the conductive tube 430 at least partially around the connection portion of the conductor wire 410 can create a heat affected zone (HAZ). The conductor wire 410 within the HAZ, in some examples, can become more brittle and/or have an increased chance of breakage than a portion of the conductor wire 410 that is not within the HAZ. The present subject matter seeks to reduce the chances of such breakage of the conductor wire 410 and/or disconnection of the conductor wire 410 from the electrode 440 in the manners described herein.

In some examples, the conductive tube 430 is compressed into direct contact with the conductor wire 410. That is, in some examples, sides of the conductive tube 430 are pushed together to trap at least a portion of the conductor wire 410, and, namely, the connection portion of the conductor wire 410, between the sides of the conductive tube 430, to thereby at least mechanically couple the conductor wire 410 to the conductive tube 430. In some examples, the conductive tube 430 is compressed such that the electrode 440 formed is substantially T-shaped. In some examples, the electrode 440 includes a substantially flat surface 444 configured to contact and stimulate tissue (including one or more of muscle tissue, nervous tissue, epithelial tissue, and/or connective tissue) of a patient and/or sense a physiological signal or condition. In some examples, the conductive tube 430 is compressed to form the T-shape with the conductor wire 410 disposed within a leg 445 of the T-shape extending from the portion of the T-shape that forms the substantially flat surface 444. In some examples, the conductor wire 410 is disposed at an end of the leg 445 of the T-shape.

In some examples, the T-shaped conductive tube 430 forms the finished electrode 440. In other examples, the T-shaped conductive tube 430 is further formed, folded, and/or manipulated into the intended shape for the electrode 440, depending upon space constraints, a geometry, a size, a purpose, etc. of a device within which the electrode 440 is to be used. As such, other shapes of the electrode are contemplated in other examples, at least some of which are described herein.

In some examples, the conductive tube 430 includes an inner surface 434 facing inwardly from the conductive tube 430 and an outer surface 436 facing outwardly from the conductive tube 430. In some examples, the connection portion of the conductor wire 410 is coupled to a first portion 434A of the inner surface 434. In some examples, the electrode 440 includes the conductive tube 430 collapsed such that at least the first portion 434A of the inner surface 434 and the connection portion of the conductor wire 410 contacts at least a second portion 434B of the inner surface 434 to substantially sandwich the connection portion of the conductor wire 410 between the first portion 434A of the inner surface 434 and the second portion 434B of the inner surface 434. In some examples, the conductive tube 430 is folded at least partially around the connection portion of the conductor wire 410 to form the electrode 440. In some examples, the conductive tube 430 is compressed at least partially around the connection portion of the conductor wire 410 to constrain motion of the connection portion of the conductor wire 410 relative to the conductive tube 430. In some examples, the connection portion is welded at a weld 419 to the electrode 440 after the conductive tube 430 is compressed to form the electrode 440.

Welding at the weld 419 can be performed in addition to welding the connection portion of the conductor wire 410 to the conductive tube 430 prior to formation of the electrode 440, in some examples. In other examples, welding at the weld 419 can be performed instead of welding the connection portion of the conductor wire 410 to the conductive tube 430 prior to formation of the electrode 440. In some examples, the connection portion is laser welded to the electrode 440. In other examples, the connection portion is resistance welded to the electrode 440. In some examples, the weld 419 is performed at an exterior 442 of the electrode 440, the weld 419 passing through the conductive tube 430 to couple the connection portion of the conductor wire 410 to the electrode 440.

In some examples, welding can cause brittleness of the connection portion and/or the conductor wire 410 and the weld, which can be counteracted by constraining motion of the connector portion with respect to the conductive tube 430. Limiting motion of the connection portion relative to the conductive tube 430 reduces, if not eliminates, the chance of the weld, the connection portion, and/or the conductive tube 430 breaking, rupturing, or otherwise separating to disrupt the connection between the conductor wire 410 and the electrode 440 to disable the electrode 440 in the ultimate device in which the electrode 440 is used. In many cases, an implanted device (such as, for instance, an implantable lead in conjunction with an implantable pulse generator) in which an electrode fails must be explanted and replaced, which leads to increased cost and recovery due to the surgical procedure required for such explant and replacement. In other cases of temporary and/or partial implantation (for instance, a catheter temporarily implanted in order to access a location within a patient), an electrode failure can require the device to be removed and replaced with another device in order to perform the intended procedure. This can lead to increased procedure time, patient risk, and cost due to having to use multiple devices for one procedure. In this way, in some examples, the present subject matter increases the robustness of the electrode 440 and, in turn, increases reliability of the ultimate device with which the electrode 440 is being used.

Referring now to FIG. 5, the component 500 includes the electrode 540 coupled to a conductor wire 510. In some examples, the electrode 540 is formed from a conductive tube 530. In some examples, the conductive tube 530 is compressed at least partially around a connection portion 514 of the conductor wire 510 to at least partially surround and couple to the connection portion 514. In some examples, the compressing of the conductive tube 530 around the connection portion 514 mechanically couples the connection portion 514 of the conductor wire 510 to the conductive tube 530. In further examples, the compressing of the conductive tube 530 around the connection portion 514 also electrically couples the connection portion 514 of the conductor wire 510 to the conductive tube 530. Alternatively, or in addition thereto, in some examples, the connection portion 514 can be welded to the conductive tube 530 prior to compression of the conductive tube 530 at least partially around the connection portion 514 of the conductor wire 510 and/or after compression of the conductive tube 530 at least partially around the connection portion 514 of the conductor wire 510. In some examples, the connection portion 514 is laser welded to the conductive tube 530. In other examples, the connection portion 514 is resistance welded to the conductive tube 530. In this way, in some examples, the connector portion 514 of the conductor wire 510 is mechanically and electrically coupled to the conductive tube 530.

In some examples, as described above, welding of the conductor wire 510 to the conductive tube 530 prior to compression of the conductive tube 530 at least partially around the connection portion 514 of the conductor wire 510 can create a heat affected zone (HAZ). The conductor wire 510 within the HAZ, in some examples, can become more brittle and/or have an increased chance of breakage than a portion of the conductor wire 510 that is not within the HAZ. The present subject matter seeks to reduce the chances of such breakage of the conductor wire 510 and/or disconnection of the conductor wire 510 from the electrode 540 in the manners described herein.

In some examples, the conductive tube 530 is compressed into direct contact with the conductor wire 510. That is, in some examples, sides of the conductive tube 530 are pushed together to trap at least a portion of the conductor wire 510, and, namely, the connection portion 514 of the conductor wire 510, between the sides of the conductive tube 530, to thereby at least mechanically couple the conductor wire 510 to the conductive tube 530. In some examples, the conductive tube 530 is compressed such that the electrode 540 formed is substantially ring-shaped. In some examples, the electrode 540 includes a rounded surface 544 configured to contact and stimulate tissue (including one or more of muscle tissue, nervous tissue, epithelial tissue, and/or connective tissue) of a patient and/or sense a physiological signal or condition.

In some examples, the ring-shaped conductive tube 530 forms the finished electrode 540. In other examples, the ring-shaped conductive tube 530 is further formed, folded, and/or manipulated into the intended shape for the electrode 540, depending upon space constraints, a geometry, a size, a purpose, etc. of a device within which the electrode 540 is to be used. As such, other shapes of the electrode are contemplated in other examples, at least some of which are described herein.

In some examples, the conductive tube 530 includes an inner surface 534 facing inwardly from the conductive tube 530 and an outer surface 536 facing outwardly from the conductive tube 530. In some examples, the connection portion 514 of the conductor wire 510 is coupled to a first portion 536A of the outer surface 536. In some examples, the electrode 540 includes the conductive tube 530 formed such that at least the first portion 536A of the outer surface 536 wraps at least partially around the connection portion 514 of the conductor wire 510 to form a channel within which the connection portion 514 of the conductor wire 510 can be disposed. In some examples, the conductive tube 530 can be formed to wrap more than 180 degrees around the connection portion 514 of the conductor wire 510 to at least partially capture the connection portion 514 of the conductor wire 510 within the channel. In some examples, the conductive tube 530 can be formed to wrap substantially 360 degrees around the connection portion 514 of the conductor wire 510 to substantially fully capture the connection portion 514 of the conductor wire 510 within the channel. In this way, in some examples, compression of the conductive tube 530 can constrain motion of the connection portion 514 of the conductor wire 510 relative to the conductive tube 530. In some examples, the connection portion 514 is welded to the electrode 540 after the conductive tube 530 is compressed to form the electrode 540.

Welding can be performed in addition to welding the connection portion 514 of the conductor wire 510 to the conductive tube 530 prior to formation of the electrode 540, in some examples. In other examples, welding can be performed instead of welding the connection portion 514 of the conductor wire 510 to the conductive tube 530 prior to formation of the electrode 540. In some examples, the connection portion 514 is laser welded to the electrode 540. In other examples, the connection portion 514 is resistance welded to the electrode 540. In some examples, the weld is performed at an interior 543 of the electrode 540, the weld passing through the conductive tube 530 to couple the connection portion 514 of the conductor wire 510 to the electrode 540. In other examples, either instead of or in addition to the weld through the conductive tube 530 from the interior 543 of the electrode 540, the connection portion 514 of the conductor wire 510 can be welded to the electrode 540 at an exterior 542 of the electrode 540.

In some examples, welding can cause brittleness of the connection portion 514 and/or the conductor wire 510 and the weld, which can be counteracted by constraining motion of the connector portion with respect to the conductive tube 530. Limiting motion of the connection portion 514 relative to the conductive tube 530 reduces, if not eliminates, the chance of the weld, the connection portion 514, and/or the conductive tube 530 breaking, rupturing, or otherwise separating to disrupt the connection between the conductor wire 510 and the electrode 540 to disable the electrode 540 in the ultimate device in which the electrode 540 is used. In many cases, an implanted device (such as, for instance, an implantable lead in conjunction with an implantable pulse generator) in which an electrode fails must be explanted and replaced, which leads to increased cost and recovery due to the surgical procedure required for such explant and replacement. In other cases of temporary and/or partial implantation (for instance, a catheter temporarily implanted in order to access a location within a patient), an electrode failure can require the device to be removed and replaced with another device in order to perform the intended procedure. This can lead to increased procedure time, patient risk, and cost due to having to use multiple devices for one procedure. In this way, in some examples, the present subject matter increases the robustness of the electrode 540 and, in turn, increases reliability of the ultimate device with which the electrode 540 is being used.

Referring now to FIG. 6, the component 600 includes the electrode 640 coupled to a conductor wire 610. In some examples, the electrode 640 is formed from a conductive tube 630. In some examples, the conductive tube 630 is compressed at least partially around a connection portion of the conductor wire 610 to at least partially surround and couple to the connection portion. In some examples, the compressing of the conductive tube 630 around the connection portion mechanically couples the connection portion of the conductor wire 610 to the conductive tube 630. In further examples, the compressing of the conductive tube 630 around the connection portion also electrically couples the connection portion of the conductor wire 610 to the conductive tube 630. Alternatively, or in addition thereto, in some examples, the connection portion can be welded to the conductive tube 630 prior to compression of the conductive tube 630 at least partially around the connection portion of the conductor wire 610 and/or after compression of the conductive tube 630 at least partially around the connection portion of the conductor wire 610. In some examples, the connection portion is laser welded to the conductive tube 630. In other examples, the connection portion is resistance welded to the conductive tube 630. In this way, in some examples, the connector portion of the conductor wire 610 is mechanically and electrically coupled to the conductive tube 630.

In some examples, as described above, welding of the conductor wire 610 to the conductive tube 630 prior to compression of the conductive tube 630 at least partially around the connection portion of the conductor wire 610 can create a heat affected zone (HAZ). The conductor wire 610 within the HAZ, in some examples, can become more brittle and/or have an increased chance of breakage than a portion of the conductor wire 610 that is not within the HAZ. The present subject matter seeks to reduce the chances of such breakage of the conductor wire 610 and/or disconnection of the conductor wire 610 from the electrode 640 in the manners described herein.

In some examples, the conductive tube 630 is compressed into direct contact with the conductor wire 610. That is, in some examples, sides of the conductive tube 630 are pushed together to trap at least a portion of the conductor wire 610, and, namely, the connection portion of the conductor wire 610, between the sides of the conductive tube 630, to thereby at least mechanically couple the conductor wire 610 to the conductive tube 630. In some examples, the conductive tube 630 is compressed such that the electrode 640 formed is substantially flattened. That is, in some examples, the conductive tube 630 is compressed down so that an inner surface 634 facing inwardly from the conductive tube 630 substantially abuts itself along a diameter of the conductive tube 630. In some examples, the conductive tube 630 is further folded so that a portion of an outer surface 636 facing outwardly from the conductive tube 630 abuts another portion of the outer surface 636. In some examples, the conductive tube 630 is folded substantially in half in this process. In other examples, the conductive tube 630 is folded in other proportions in this process. In still other examples, the conductive tube 630 need not be further folded, such that the conductive tube 630 compressed down so that the inner surface 634 substantially abuts itself along a diameter of the conductive tube 630 forms the finished electrode 640. In some examples, the electrode 640 includes a substantially flat surface 644 configured to contact and stimulate tissue (including one or more of muscle tissue, nervous tissue, epithelial tissue, and/or connective tissue) of a patient and/or sense a physiological signal or condition. In some examples, the conductive tube 630 is compressed to form the flattened shape with the conductor wire 610 disposed at an end of the flattened conductive tube 630 of the electrode 640.

In some examples, the flattened conductive tube 630 forms the finished electrode 640. In other examples, the flattened conductive tube 630 is further formed, folded, and/or manipulated into the intended shape for the electrode 640, depending upon space constraints, a geometry, a size, a purpose, etc. of a device within which the electrode 640 is to be used. As such, other shapes of the electrode are contemplated in other examples, at least some of which are described herein.

In some examples, the connection portion of the conductor wire 610 is coupled to a first portion 634A of the inner surface 634. In some examples, the electrode 640 includes the conductive tube 630 collapsed such that at least the first portion 634A of the inner surface 634 and the connection portion of the conductor wire 610 contacts at least a second portion 634B of the inner surface 634 to substantially sandwich the connection portion of the conductor wire 610 between the first portion 634A of the inner surface 634 and the second portion 634B of the inner surface 634. In some examples, the conductive tube 630 is folded at least partially around the connection portion of the conductor wire 610 to form the electrode 640. In some examples, the conductive tube 630 is compressed at least partially around the connection portion of the conductor wire 610 to constrain motion of the connection portion of the conductor wire 610 relative to the conductive tube 630. In some examples, the connection portion is welded to the electrode 640 after the conductive tube 630 is compressed to form the electrode 640.

Welding can be performed in addition to welding the connection portion of the conductor wire 610 to the conductive tube 630 prior to formation of the electrode 640, in some examples. In other examples, welding can be performed instead of welding the connection portion of the conductor wire 610 to the conductive tube 630 prior to formation of the electrode 640. In some examples, the connection portion is laser welded to the electrode 640. In other examples, the connection portion is resistance welded to the electrode 640. In some examples, the weld is performed at an exterior 642 of the electrode 640, the weld passing through the conductive tube 630 to couple the connection portion of the conductor wire 610 to the electrode 640.

In some examples, welding can cause brittleness of the connection portion and/or the conductor wire 610 and the weld, which can be counteracted by constraining motion of the connector portion with respect to the conductive tube 630. Limiting motion of the connection portion relative to the conductive tube 630 reduces, if not eliminates, the chance of the weld, the connection portion, and/or the conductive tube 630 breaking, rupturing, or otherwise separating to disrupt the connection between the conductor wire 610 and the electrode 640 to disable the electrode 640 in the ultimate device in which the electrode 640 is used. In many cases, an implanted device (such as, for instance, an implantable lead in conjunction with an implantable pulse generator) in which an electrode fails must be explanted and replaced, which leads to increased cost and recovery due to the surgical procedure required for such explant and replacement. In other cases of temporary and/or partial implantation (for instance, a catheter temporarily implanted in order to access a location within a patient), an electrode failure can require the device to be removed and replaced with another device in order to perform the intended procedure. This can lead to increased procedure time, patient risk, and cost due to having to use multiple devices for one procedure. In this way, in some examples, the present subject matter increases the robustness of the electrode 640 and, in turn, increases reliability of the ultimate device with which the electrode 640 is being used.

Referring to FIG. 7, in some examples, as described herein, the presently-described subject matter can be used in a medical device 700. That is, one or more electrodes 740 can be disposed within the medical device 700, the medical device 700 being configured for at least partial implantation within a patient. Although the medical device 700 of FIG. 7 includes three electrodes 740, this is merely illustrative. In various examples, the medical device 700 can include more or fewer than three electrodes 740 depending upon the application for which the medical device 700 is to be used.

The medical device 700, in some examples, can include an elongate medical device 700 including an elongate body 702 including a distal end 702A and a proximal end 702B. In various examples, the elongate medical device 700 can include an elongate lead; an elongate catheter, introducer, sheath, or the like; a guidewire; etc. In some examples, the one or more electrodes 740 are disposed proximate the distal end 702A of the medical device 700. In some examples, the one or more electrodes 740 are connected by conductor wires 710 to a corresponding number of contacts 760. In some examples, the one or more contacts 760 are disposed proximate the distal end 702B of the medical device 700. The one or more contacts 760, in some examples, are configured to electrically couple with another medical device (not shown), such as, for instance, a pulse generator, a medical monitor, a mapping device, or the like, either implantable or external, to, in turn, electrically couple the one or more electrodes 740 to the pulse generator, a medical monitor, a mapping device, etc. and enable the one or more electrodes 740 to stimulate tissue (including one or more of muscle tissue, nervous tissue, epithelial tissue, and/or connective tissue) of a patient and/or sense a physiological signal or condition of the patient.

In some examples, the one or more electrodes 740 are each disposed within the medical device 700 with at least an electrode surface 744 being exposed to an exterior of the medical device 700. In some examples, the electrode surface 744 of each of the one or more electrodes 740 is a rounded surface 744 configured to contact and stimulate tissue of a patient and/or sense a physiological signal or condition. In various examples, the one or more electrodes 740 can be similarly shaped to one or more of the examples of electrodes described above, such as, but not limited the electrodes 240, 340, 540. In other examples, the one or more electrodes 740 can have rounded surfaces 744 differently shaped from those of the electrodes 240, 340, 540, provided the medical device 700 is capable of properly functioning for the application for which the medical device 700 is being used.

Referring to FIG. 8, in some examples, as described herein, the presently-described subject matter can be used in a medical device 800. That is, one or more electrodes 840 can be disposed within the medical device 800, the medical device 800 being configured for at least partial implantation within a patient. Although the medical device 800 of FIG. 8 includes three electrodes 840, this is merely illustrative. In various examples, the medical device 800 can include more or fewer than three electrodes 840 depending upon the application for which the medical device 800 is to be used.

The medical device 800, in some examples, can include an elongate medical device 800 including an elongate body 802 including a distal end 802A and a proximal end 802B. In various examples, the elongate medical device 800 can include an elongate lead; an elongate catheter, introducer, sheath, or the like; a guidewire; etc. In some examples, the one or more electrodes 840 are disposed proximate the distal end 802A of the medical device 800. In some examples, the one or more electrodes 840 are connected by conductor wires 810 to a corresponding number of contacts 860. In some examples, the one or more contacts 860 are disposed proximate the distal end 802B of the medical device 800. The one or more contacts 860, in some examples, are configured to electrically couple with another medical device (not shown), such as, for instance, a pulse generator, a medical monitor, a mapping device, or the like, either implantable or external, to, in turn, electrically couple the one or more electrodes 840 to the pulse generator, a medical monitor, a mapping device, etc. and enable the one or more electrodes 840 to stimulate tissue (including one or more of muscle tissue, nervous tissue, epithelial tissue, and/or connective tissue) of a patient and/or sense a physiological signal or condition of the patient.

In some examples, the one or more electrodes 840 are each disposed within the medical device 800 with at least an electrode surface 844 being exposed to an exterior of the medical device 800. In some examples, the electrode surface 844 of each of the one or more electrodes 840 is a substantially flat surface 844 configured to contact and stimulate tissue of a patient and/or sense a physiological signal or condition. In various examples, the one or more electrodes 840 can be similarly shaped to one or more of the examples of electrodes described above, such as, but not limited the electrodes 140, 440, 640. In other examples, the one or more electrodes 840 can have substantially flat surfaces 844 differently shaped from those of the electrodes 140, 440, 640, provided the medical device 800 is capable of properly functioning for the application for which the medical device 800 is being used.

Figure 9:
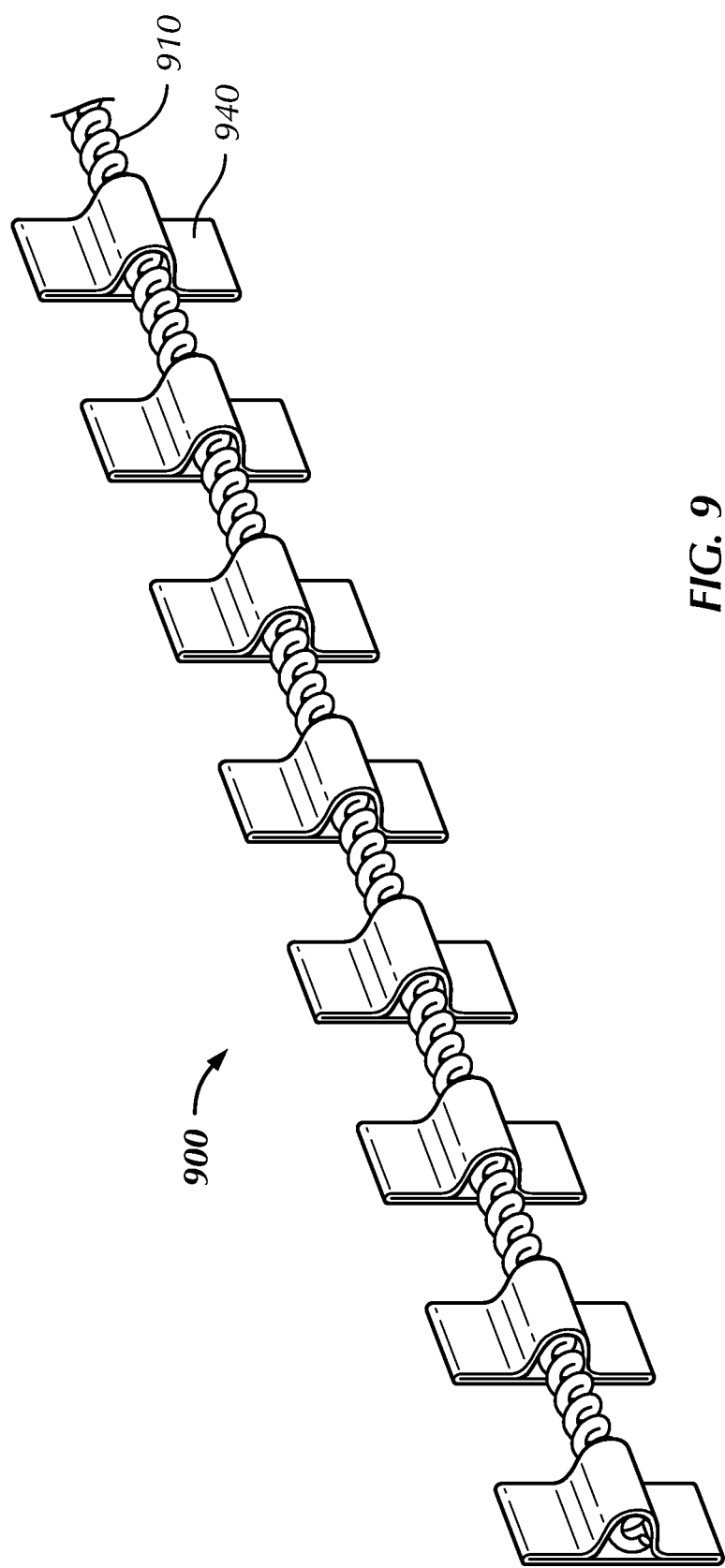
FIG. 9 is a perspective view of electrodes are formed around a conductor in accordance with at least one example of the invention.

Referring to FIG. 9, an assembly 900 includes one or more components or electrodes 940. In the example shown in FIG. 9, the assembly 900 includes eight electrodes 940; however, this is merely illustrative as the assembly 900, in other examples, can include more or less than eight electrodes 940. In some examples, the one or more electrodes 940 can be similar to one or more of the example electrodes 140, 240, 340A, 340B, 340C, 440, 540, 640, 740, 840 described above, and, as such, various aspects of the description of the electrodes 140, 240, 340A, 340B, 340C, 440, 540, 640, 740, 840 above can also apply to the one or more electrodes 940. In some examples, a conductor coil 910 is coupled to the one or more electrodes 940. In some examples, the electrodes 940 are formed around the conductor coil 910 and then welded (laser or resistance welded, for instance) to the conductor coil 910. In some examples, all of the electrodes 940 are connected to a single conductor wire of the conductor coil 910. In other examples, the conductor coil 910 is formed from multiple conductors with a different conductor being attached to each of the electrodes 940. In some examples, with the one or more electrodes 940 of the assembly 900 used in an at least partially implantable elongate member such as, but not limited to, a catheter, a sheath, an introducer, a lead, a guidewire, or the like, the one or more electrodes 940 of the assembly 900 can be used to stimulate tissue (including one or more of muscle tissue, nervous tissue, epithelial tissue, and/or connective tissue), sense physiological conditions, or a combination thereof.

Figure 10A:
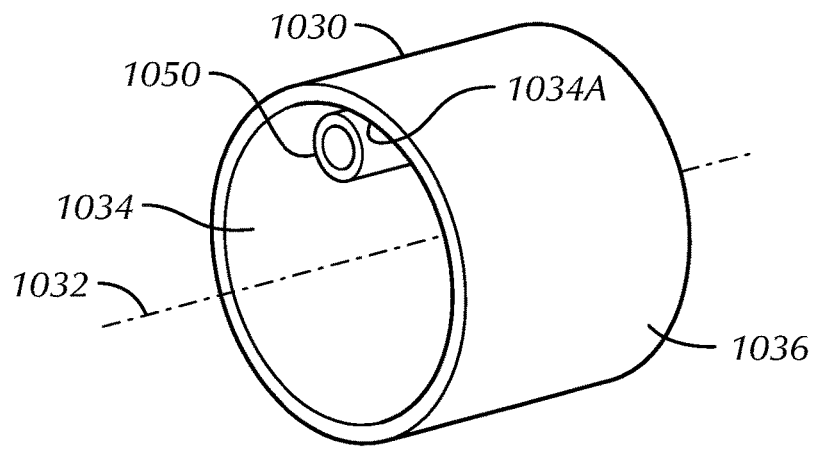
FIGS. 10A-10C show formation of an electrode in accordance with at least one example of the invention.
Figure 10B:
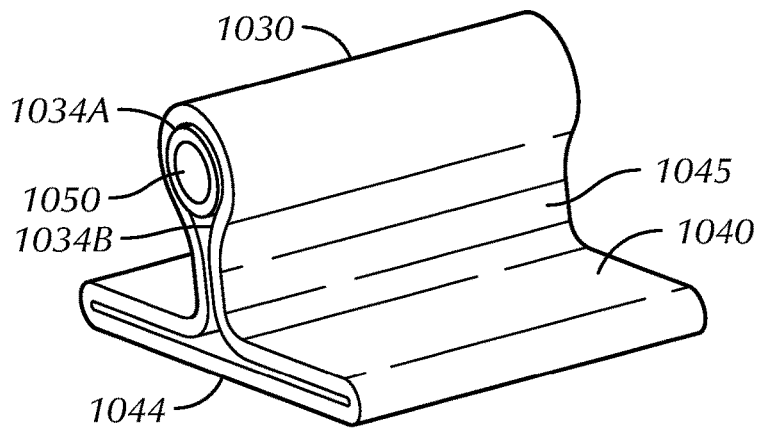
Figure 10C:
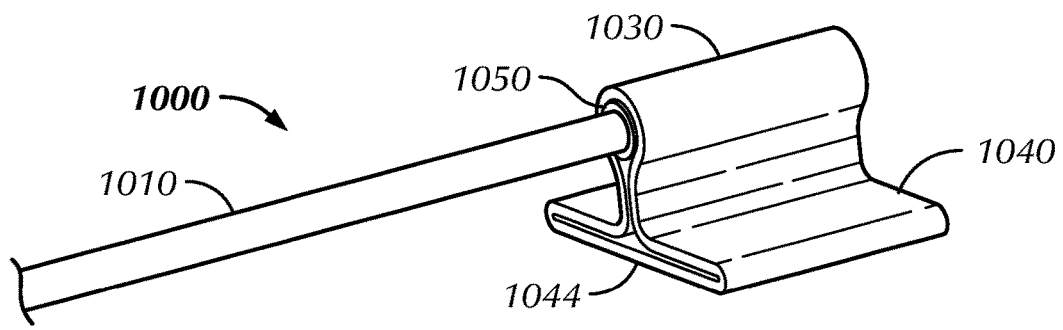

Referring now to FIGS. 10A-10C, in some examples, a component 1000 includes an electrode 1040 coupled to a conductor wire 1010. In some examples, the electrode 1040 is formed from a conductive tube 1030. In some examples, the conductive tube 1030 is compressed at least partially around a coupling tube 1050. In some examples, the conductive tube 1030 is compressed into direct contact with the coupling tube 1050. In some examples, the conductive tube 1030 is folded at least partially around the coupling tube 1050 within which the connection portion of the conductor wire 1010 can be disposed to form the electrode 1040. In some examples, the conductive tube 1030 is crimped around the coupling tube 1050 to couple the coupling tube 1050 to the conductive tube 1030. In some examples, the conductive tube 1030 is welded to the coupling tube 1050 to couple the coupling tube 1050 to the conductive tube 1030, either in addition to, or instead of, crimping the conductive tube 1030 at least partially around the coupling tube 1050. In some examples, the conductive tube 1030 includes an inner surface 1034 facing inwardly toward an axis 1032 of the conductive tube 1030 and an outer surface 1036 facing outwardly away from the axis 1032 of the conductive tube 1030. In some examples, the coupling tube 1050 is coupled to a first portion 1034A of the inner surface 1034. In some examples, the electrode 1040 includes the conductive tube 1030 collapsed such that at least the first portion 1034A of the inner surface 1034 and the coupling tube 1050 contact at least a second portion 1034B of the inner surface 1034 to substantially sandwich the coupling tube 1050 between the first portion 1034A of the inner surface 1034 and the second portion 1034B of the inner surface 1034.

The coupling tube 1050, in some examples, is configured to accept the conductor wire 1010 within the coupling tube 1050, such that a connection portion of the conductor wire 1010 is at least partially disposed within the coupling tube 1050 of the completed component 1000. In some examples, the conductor wire 1010 is coupled to the coupling tube 1050. In some examples, the coupling tube 1050 can be crimped onto the conductor wire 1010. In other examples, the conductor wire 1010 can be welded to the coupling tube 1050, in addition to, or instead of, crimping the conductor wire 1010 to the coupling tube 1050. In some examples, the connection portion of the conductor wire 1010 is laser welded to the coupling tube 1050. In other examples, the connection portion of the conductor wire 1010 is resistance welded to the coupling tube 1050. In this way, the connection portion of the conductor wire 1010 is mechanically and electrically coupled to the coupling tube 1050, which, in turn, is mechanically and/or electrically coupled to the conductive tube 1030.

In some examples, the conductive tube 1030 is compressed such that the electrode 1040 formed is substantially T-shaped. In some examples, the electrode 1040 includes a substantially flat surface 1044 configured to contact and stimulate tissue (including one or more of muscle tissue, nervous tissue, epithelial tissue, and/or connective tissue) of a patient and/or sense a physiological signal or condition. In some examples, the conductive tube 1030 is compressed to form the T-shape with the coupling tube 1050 disposed within a leg 1045 of the T-shape extending from the portion of the T-shape that forms the substantially flat surface 1044. In some examples, the coupling tube 1050 is disposed at an end of the leg 1045 of the T-shape.

In some examples, the T-shaped conductive tube 1030 forms the finished electrode 1040. In other examples, the T-shaped conductive tube 1030 is further formed, folded, and/or manipulated into the intended shape for the electrode 1040, depending upon space constraints, a geometry, a size, a purpose, etc. of a device within which the electrode 1040 is to be used. As such, other shapes of the electrode are contemplated in other examples, at least some of which are described herein.

In this way, in some examples, the electrode 1040 with the coupling tube 1050 can reduce, if not eliminate, the need for welding to form the component 1000, which, in turn, reduces, if not eliminates, the effects of a heat affected zone (HAZ), as described above with respect to other examples of components. In examples where welding is used, brittleness (of the weld, the conductor wire 1010, etc.) caused can be counteracted by constraining motion of the connector portion of the conductor wire 1010 with respect to the conductive tube 1030 and/or the coupling tube 1050. Limiting motion of the connection portion relative to the conductive tube 1030 and/or the coupling tube 1050 reduces, if not eliminates, the chance of the weld, the connection portion, the conductive tube 1030, and/or the coupling tube 1050 breaking, rupturing, or otherwise separating to disrupt the connection between the conductor wire 1010 and the electrode 1040, leading to the disabling of the electrode 1040 in the ultimate device in which the electrode 1040 is used. In many cases, an implanted device (such as, for instance, an implantable lead in conjunction with an implantable pulse generator) in which an electrode fails must be explanted and replaced, which leads to increased cost and recovery due to the surgical procedure required for such explant and replacement. In other cases of temporary and/or partial implantation (for instance, a catheter temporarily implanted in order to access a location within a patient), an electrode failure can require the device to be removed and replaced with another device in order to perform the intended procedure. This can lead to increased procedure time, patient risk, and cost due to having to use multiple devices for one procedure. In this way, in some examples, the present subject matter increases the robustness of the electrode 1040 and, in turn, increases reliability of the ultimate device with which the electrode 1040 is being used.

Although the coupling tube 1050 is presently described as being used with the T-shaped electrode 1040, in other examples, it is contemplated that the coupling tube 1050 can be used with an electrode having a shape other than a T-shape, such as, but not limited to, the examples of the electrodes 140, 240, 340A, 340B, 340C, 540, 640, 740, 840, 940 described herein. As such, electrodes of other shapes can benefit from the inclusion of a coupling tube by reducing, if not eliminating welds to reduce, if not eliminate, the adverse effects of HAZ within the electrodes to thereby facilitate a more robust electrode in a finished medical device.

Figure 11A:
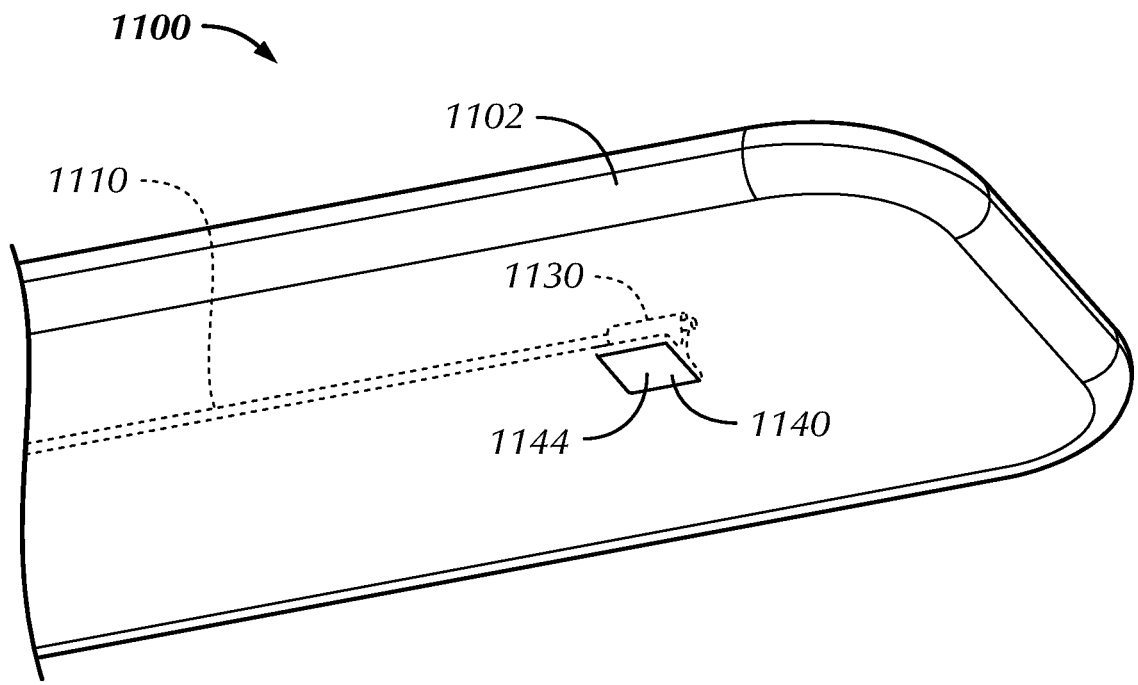
FIG. 11A is a perspective view of a lead including an electrode in accordance with at least one example of the invention.
Figure 11B:
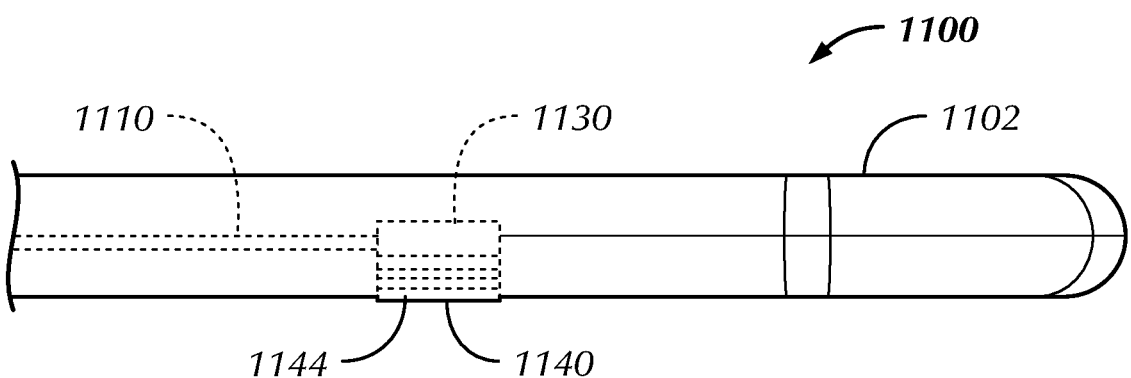
FIG. 11B is a side view of a lead including an electrode in accordance with at least one example of the invention.

Referring to FIGS. 11A and 11B, in some examples, as described herein, the presently-described subject matter can be used in a medical device 1100. That is, one or more electrodes 1140 can be disposed within the medical device 1100, the medical device 1100 being configured for at least partial implantation within a patient. Although the medical device 1100 of FIGS. 11A and 11B includes one electrode 1140, this is merely illustrative. In various examples, the medical device 1100 can include more than one electrode 1140 depending upon the application for which the medical device 1100 is to be used. In some examples, the electrode 1140 is formed from a conductive tube 1130 in a manner similar to that described above with respect to the electrode 1040. In some examples, the electrode 1140 can include a coupling tube similar to the coupling tube 1050 described above. In other examples, the electrode 1140 can include no coupling tube and instead have direct coupling between a conductor wire 1110 and the conductive tube 1130.

In various examples, the elongate medical device 1100 can include a paddle lead, a cuff lead, or the like. In some examples, the medical device 1100 includes a body 1102 at least partially surrounding the one or more electrodes 1140. In some examples, the body 1102 is formed, at least in part, from silicone. In other examples, the body 1102 can be formed from one or more other biocompatible materials.

In some examples, the one or more electrodes 1140 are disposed proximate a distal end of the medical device 1100. In some examples, the one or more electrodes 1140 are connected by one or more conductor wires 1110 to a corresponding number of contacts at a proximal end of the medical device 1100. The one or more contacts, in some examples, are configured to electrically couple with another medical device (not shown), such as, for instance, a pulse generator, a medical monitor, a mapping device, or the like, either implantable or external, to, in turn, electrically couple the one or more electrodes 1140 to the pulse generator, a medical monitor, a mapping device, etc. and enable the one or more electrodes 1140 to stimulate tissue (including one or more of muscle tissue, nervous tissue, epithelial tissue, and/or connective tissue) of a patient and/or sense a physiological signal or condition of the patient.

In some examples, the one or more electrodes 1140 are each disposed within the medical device 1100 with at least an electrode surface 1144 being exposed to an exterior of the medical device 1100. In some examples, the electrode surface 1144 of each of the one or more electrodes 1140 is a substantially flat surface 1144 configured to contact and stimulate tissue of a patient and/or sense a physiological signal or condition. In various examples, the one or more electrodes 1140 can be similarly shaped to one or more of the examples of electrodes described above, such as, but not limited the electrodes 140, 440, 640, 840, 940, 1040. In other examples, the one or more electrodes 1140 can have substantially flat surfaces 1144 differently shaped from those of the electrodes 140, 440, 640, 840, 940, 1040, provided the medical device 1100 is capable of properly functioning for the application for which the medical device 1100 is being used. In still other examples, the one or more electrodes 1140 can have rounded surfaces shaped similarly to those of the electrodes 240, 340, 540.

In some examples and with reference to FIGS. 1-11B, the present subject matter includes a method of forming a component 100, 200, 300A, 300B, 300C, 400, 500, 600, 1000 or an assembly 300, 900 for a medical device 700, 800, 1100. In some examples, a connection portion 114, 214, 314A, 314B, 314C, 514 of a conductor wire 110, 210, 310A, 310B, 310C, 410, 510, 610, 710, 810, 910, 1010, 1110 is operably coupled to a conductive tube 130, 230, 330A, 330B, 330C, 430, 530, 630, 1030, 1130. In some examples, the connection portion 114, 214, 314A, 314B, 314C, 514 of the conductor wire 110, 210, 310A, 310B, 310C, 410, 510, 610, 710, 810, 910, 1010, 1110 is placed in contact with the conductive tube 130, 230, 330A, 330B, 330C, 430, 530, 630, 1030, 1130. In some examples, the connection portion 114, 214, 314A, 314B, 314C, 514 of the conductor wire 110, 210, 310A, 310B, 310C, 410, 510, 610, 710, 810, 910, 1110 is placed in direct contact with the conductive tube 130, 230, 330A, 330B, 330C, 430, 530, 630, 1130. In other examples, the connection portion 114, 214, 314A, 314B, 314C, 514 of the conductor wire 110, 210, 310A, 310B, 310C, 410, 510, 610, 710, 810, 910, 1010, 1110 is placed in direct contact with a coupling tube 1050 in contact with the conductive tube 130, 230, 330A, 330B, 330C, 430, 530, 630, 1030, 1130. In some examples, the conductor wire 110, 210, 310A, 310B, 310C, 410, 610, 710, 810, 910, 1010, 1110 is placed in contact with an inner surface 134, 434, 634, 1034 of the conductive tube 130, 230, 330A, 330B, 330C, 430, 630, 1030, 1130. In other examples, the conductor wire 510, 710, 810 is placed in contact with an outer surface 536 of the conductive tube 530.

In some examples, an electrode 140, 240, 340A, 340B, 340C, 440, 540, 640, 740, 840, 940, 1040, 1140 is formed by compressing the conductive tube 130, 230, 330A, 330B, 330C, 430, 530, 630, 1030, 1130 at least partially around the connection portion 114, 214, 314A, 314B, 314C, 514 of the conductor wire 110, 210, 310A, 310B, 310C, 410, 510, 610, 710, 810, 910, 1010, 1110 to at least partially surround and couple to the connection portion 114, 214, 314A, 314B, 314C, 514. In some examples, the connection portion 114, 214, 314A, 314B, 314C, 514 of the conductor wire 110, 210, 310A, 310B, 310C, 410, 510, 610, 710, 810, 910, 1010, 1110 is welded to the electrode 140, 240, 340A, 340B, 340C, 440, 540, 640, 740, 840, 940, 1040, 1140. In some further examples, the connection portion 114, 214, 314A, 314B, 314C, 514 is laser welding to the electrode 140, 240, 340A, 340B, 340C, 440, 540, 640, 740, 840, 940, 1040, 1140. In other examples, the connection portion 114, 214, 314A, 314B, 314C, 514 is resistance welded to the electrode 140, 240, 340A, 340B, 340C, 440, 540, 640, 740, 840, 940, 1040, 1140. In other examples, the connection portion 114, 214, 314A, 314B, 314C, 514 is mechanically coupled to the electrode 140, 240, 340A, 340B, 340C, 440, 540, 640, 740, 840, 940, 1040, 1140 with the compression of the conductive tube 130, 230, 330A, 330B, 330C, 430, 530, 630, 1030, 1130 at least partially around the connection portion 114, 214, 314A, 314B, 314C, 514 of the conductor wire 110, 210, 310A, 310B, 310C, 410, 510, 610, 710, 810, 910, 1010, 1110. In further examples, the compressing of the conductive tube 130, 230, 330A, 330B, 330C, 430, 530, 630, 1030,

1130 around the connection portion 114, 214, 314A, 314B, 314C, 514 also electrically couples the connection portion 114, 214, 314A, 314B, 314C, 514 of the conductor wire 110, 210, 310A, 310B, 310C, 410, 510, 610, 710, 810, 910, 1010, 1110 to the conductive tube 130, 230, 330A, 330B, 330C, 430, 530, 630, 1030, 1130. In this way, in some examples, the connector portion 114, 214, 314A, 314B, 314C, 514 of the conductor wire 110, 210, 310A, 310B, 310C, 410, 510, 610, 710, 810, 910, 1010, 1110 is mechanically and electrically coupled to the conductive tube 130, 230, 330A, 330B, 330C, 430, 530, 630, 1030, 1130.

In some examples, the electrode 140, 240, 340A, 340B, 340C, 440, 540, 640, 740, 840, 940, 1040, 1140 is formed by compressing the conductive tube 130, 230, 330A, 330B, 330C, 430, 530, 630, 1030, 1130 at least partially around the coupling tube 1050, within which is disposed the connection portion 114, 214, 314A, 314B, 314C, 514 of the conductor wire 110, 210, 310A, 310B, 310C, 410, 510, 610, 710, 810, 910, 1010, 1110, to at least partially surround and couple to the coupling tube 1050 and, in turn, the connection portion 114, 214, 314A, 314B, 314C, 514. In some examples, the electrode 140, 240, 340A, 340B, 340C, 440, 540, 640, 740, 840, 940, 1040, 1140 is formed by compressing the conductive tube 130, 230, 330A, 330B, 330C, 430, 530, 630, 1030, 1130 into direct contact with a coupling tube 1050, the conductor wire 110, 210, 310A, 310B, 310C, 410, 510, 610, 710, 810, 910, 1010, 1110 being at least partially disposed within the coupling tube 1050. In some examples, the conductor wire 110, 210, 310A, 310B, 310C, 410, 510, 610, 710, 810, 910, 1010, 1110 is coupled to the coupling tube 1050. In further examples, the conductor wire 110, 210, 310A, 310B, 310C, 410, 510, 610, 710, 810, 910, 1010, 1110 is welded to the coupling tube 1050. In some examples, the conductor wire 110, 210, 310A, 310B, 310C, 410, 510, 610, 710, 810, 910, 1010, 1110 is laser welded to the coupling tube 1050. In other examples, the conductor wire 110, 210, 310A, 310B, 310C, 410, 510, 610, 710, 810, 910, 1010, 1110 is resistance welded to the coupling tube 1050.

In some examples, the electrode 140, 240, 340A, 340B, 340C, 440, 540, 640, 740, 840, 940, 1040, 1140 is formed by compressing the conductive tube 130, 230, 330A, 330B, 330C, 430, 530, 630, 1030, 1130 at least partially around the connection portion 114, 214, 314A, 314B, 314C, 514 of the conductor wire 110, 210, 310A, 310B, 310C, 410, 510, 610, 710, 810, 910, 1010, 1110 to constrain motion of the connection portion 114, 214, 314A, 314B, 314C, 514 of the conductor wire 110, 210, 310A, 310B, 310C, 410, 510, 610, 710, 810, 910, 1010, 1110 relative to the conductive tube 130, 230, 330A, 330B, 330C, 430, 530, 630, 1030, 1130.

In some examples, the conductive tube 130, 230, 330A, 330B, 330C, 430, 530, 630, 1030, 1130 includes an inner surface 134, 434, 534, 634, 1034 facing inwardly toward an axis 132, 1032 of the conductive tube 130, 230, 330A, 330B, 330C, 430, 530, 630, 1030, 1130 and an outer surface 136, 436, 536, 636, 1036 facing outwardly away from the axis 132, 1032 of the conductive tube 130, 230, 330A, 330B, 330C, 430, 530, 630, 1030, 1130. In some examples, the connection portion 114, 214, 314A, 314B, 314C of the conductor wire 110, 210, 310A, 310B, 310C, 410, 610, 710, 810, 910, 1010, 1110 is coupled to a first portion 134A, 434A, 634A, 1034A of the inner surface 134, 434, 634, 1034. Compressing the conductive tube 130, 230, 330A, 330B, 330C, 430, 530, 630, 1030, 1130, in some examples, causes the at least first portion 134A, 434A, 634A, 1034A of the inner surface 134, 434, 634, 1034 and the connection portion 114, 214, 314A, 314B, 314C of the conductor wire 110, 210, 310A, 310B, 310C, 410, 610, 710, 810, 910, 1010, 1110 to contact at least a second portion 134B, 434B, 634B, 1034B of the inner surface 134, 434, 634, 1034 to substantially sandwich the connection portion 114, 214, 314A, 314B, 314C of the conductor wire between the first portion 134A, 434A, 634A, 1034A of the inner surface 134, 434, 634, 1034 and the second portion 134B, 434B, 634B, 1034B of the inner surface 134, 434, 634, 1034. In some examples, the connection portion 514 of the conductor wire 510 is coupled to a first portion 536A of the outer surface 536 and the conductive tube 530 is compressed such that the first portion 536A of the outer surface 536 wraps at least partially around the connection portion 514 of the conductor wire 510 to form a channel within which the connection portion 514 of the conductor wire 510 can be disposed. In other examples, the conductive tube 130, 230, 330A, 330B, 330C, 430, 530, 630, 1030, 1130 or the electrode 740, 840, 940 is compressed around and coupled to the coupling tube 1050, which, in turn, is coupled to the connection portion 114, 214, 314A, 314B, 314C, 514 of the conductor wire 110, 210, 310A, 310B, 310C, 410, 510, 610, 710, 810, 910, 1010, 1110. In some examples, an axial extent of the conductive tube 130, 230, 330A, 330B, 330C, 430, 530, 630, 1030, 1130, the electrode 740, 840, 940, and/or the coupling tube 1050 is deformed to contact itself, sandwiching the connector portion 114, 214, 314A, 314B, 314C, 514 of the conductor wire 110, 210, 310A, 310B, 310C, 410, 510, 610, 710, 810, 910, 1010, 1110 in between. That is, from a first edge (such as a proximal edge) to a second edge (such as a distal edge), the conductive tube 130, 230, 330A, 330B, 330C, 430, 530, 630, 1030, 1130 is deformed so that spaced apart portions of the first edge are compressed together to contact each other, spaced apart portions of the second edge are compressed together to contact each other, and spaced apart portions disposed axially in between the first edge and the second edge are compressed together to contact each other.

In some examples, the electrode 140, 240, 340A, 340B, 340C, 740, 840 is formed by compressing the conductive tube 130, 230, 330A, 330B, 330C such that the electrode 140, 240, 340A, 340B, 340C, 740, 840 formed is substantially U-shaped. In other examples, the electrode 440, 840, 940, 1040, 1140 is formed by compressing the conductive tube 430, 1030, 1130 such that the electrode 440, 840, 940, 1040, 1140 formed is substantially T-shaped. In still other examples, the electrode 540, 640 is formed into other shapes, such as substantially flattened, substantially ring-shaped, or the like. In some examples, the electrode 140, 240, 340A, 340B, 340C, 440, 540, 640, 740, 840, 940, 1140 is formed by compressing the conductive tube 130, 230, 330A, 330B, 330C, 430, 530, 630, 1130 into direct contact with the conductor wire 110, 210, 310A, 310B, 310C, 410, 510, 610, 710, 810, 910, 1110.

In various examples, the conductive tube 130, 230, 330A, 330B, 330C, 430, 530, 630, 1030, 1130 and/or the electrode 740, 840, 940, can be formed from or otherwise include one or of platinum; a platinum alloy, such as, but not limited to, a platinum-iridium alloy; gold; a gold alloy; a nickel-cobalt alloy, such as, but not limited to, MP35N; stainless steel; and/or other biocompatible materials capable of conducting electrical signals. In various examples, the coupling tube 1050 can be formed from or otherwise include one or of platinum; a platinum alloy, such as, but not limited to, a platinum-iridium alloy; gold; a gold alloy; a nickel-cobalt alloy, such as, but not limited to, MP35N; stainless steel; and/or other biocompatible materials capable of conducting electrical signals. In some examples, the coupling tube 1050 can be formed from the same one or more materials as the conductive tube 130, 230, 330A, 330B, 330C, 430, 530, 630, 1030, 1130 and/or the electrode 740, 840, 940. In other examples, the coupling tube 1050 can be formed from the one or more materials that are different from the one or more material of the conductive tube 130, 230, 330A, 330B, 330C, 430, 530, 630, 1030, 1130 and/or the electrode 740, 840, 940. In various examples, the conductor wire 110, 210, 310A, 310B, 310C, 410, 510, 610, 710, 810, 910, 1010, 1110 can be formed from or otherwise include one of or nickel; a nickel-cobalt alloy, such as, but not limited to, MP35N and/or a drawn tube including a MP35N tube with a silver core; platinum; a platinum alloy, such as, but not limited to, a platinum-iridium alloy; stainless steel; and/or other biocompatible materials capable of conducting electrical signals.

The present inventors have recognized various advantages of the subject matter described herein. The present inventors have recognized, among other things, that the present subject matter can be used in a device to connect a conductor wire to an electrode. Such a device includes, but is not limited to, a medical device. In various examples, the present subject matter is advantageous in that it provides for a connection between the conductor wire and the electrode in a manner that can inhibit premature breakage of the conductor wire or breakage of the conductor wire from the electrode. In some examples, the present subject matter inhibits breakage of the conductor wire and/or the connection between the conductor wire and the electrode within the HAZ. While various advantages of the example systems are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. A component for a medical device, the component comprising:
    a conductor wire including a connection portion; and
    an electrode formed from a conductive tube, wherein the conductive tube is compressed at least partially around the connection portion of the conductor wire to at least partially surround and couple to the connection portion, the electrode including:
        a flattened portion including a substantially flat surface configured to contact and stimulate tissue; and
        a leg extending from the flattened portion of the electrode, the flattened portion and the leg substantially forming a T-shape, wherein the connection portion of the conductor wire is disposed within the leg of the electrode.

2. The component of claim 1, wherein the connection portion of the conductor wire is disposed proximate a distal end of the conductor wire.

3. The component of claim 1, wherein the connection portion is welded to the electrode.

4. The component of claim 1, wherein the medical device includes an elongate lead, wherein the electrode is disposed within the lead with at least an electrode surface being exposed to an exterior of the lead.

5. The component of claim 1, wherein the medical device includes an elongate catheter, wherein the electrode is disposed within the catheter with at least an electrode surface being exposed to an exterior of the catheter.

6. The component of claim 1, wherein the conductive tube is compressed into direct contact with the conductor wire.

7. The component of claim 1, comprising a coupling tube, wherein the conductive tube is compressed into direct contact with the coupling tube, the conductor wire being at least partially disposed within the coupling tube.

8. The component of claim 1, wherein the conductive tube is compressed at least partially around the connection portion of the conductor wire to constrain motion of the connection portion of the conductor wire relative to the conductive tube.

9. A component for a medical device, the component comprising:
    a conductor wire including a connection portion; and
    an electrode formed from a conductive tube, wherein the conductive tube includes an inner surface facing inwardly toward an axis of the conductive tube and an outer surface facing outwardly away from the axis of the conductive tube, the connection portion of the conductor wire being coupled to a first portion of the inner surface, wherein the electrode includes the conductive tube collapsed such that at least the first portion of the inner surface and the connection portion of the conductor wire contacts at least a second portion of the inner surface to substantially sandwich the connection portion of the conductor wire between the first portion of the inner surface and the second portion of the inner surface, the electrode including:
- a flattened portion including a substantially flat surface configured to contact and stimulate tissue; and
- a leg extending outwardly from the flattened portion of the electrode, the flattened portion and the leg substantially forming a T-shape, wherein the connection portion of the conductor wire is disposed within the leg of the electrode.

10. The component of claim 9, wherein the connection portion is welded to the electrode.

11. The component of claim 9, wherein the connection portion of the conductor wire is disposed proximate a distal end of the conductor wire.

12. The component of claim 9, wherein the conductive tube is compressed into direct contact with the conductor wire.

13. The component of claim 9, comprising a coupling tube, wherein the conductive tube is compressed into direct contact with the coupling tube, the conductor wire being at least partially disposed within the coupling tube.

14. The component of claim 9, wherein the conductive tube is compressed at least partially around the connection portion of the conductor wire to constrain motion of the connection portion of the conductor wire relative to the conductive tube.

15. A component for a medical device, the component comprising:
- a conductor wire including a connection portion; and
- an electrode formed from a conductive tube, wherein the conductive tube is compressed at least partially around the connection portion of the conductor wire to at least partially surround and couple to the connection portion, the electrode including:
  - a flattened portion including a substantially flat surface configured to contact and stimulate tissue; and
  - a protrusion extending from the flattened portion of the electrode, the flattened portion and the protrusion substantially forming a T-shape, wherein the connection portion of the conductor wire is disposed within the protrusion of the electrode.

16. The component of claim 15, wherein the connection portion of the conductor wire is disposed proximate a distal end of the conductor wire.

17. The component of claim 15, wherein the connection portion is welded to the electrode.

18. The component of claim 15, wherein the conductive tube is compressed into direct contact with the conductor wire.

19. The component of claim 15, comprising a coupling tube, wherein the conductive tube is compressed into direct contact with the coupling tube, the conductor wire being at least partially disposed within the coupling tube.

20. The component of claim 15, wherein the conductive tube is compressed at least partially around the connection portion of the conductor wire to constrain motion of the connection portion of the conductor wire relative to the conductive tube.

* * * * *